(12) United States Patent
Bao et al.

(10) Patent No.: US 11,707,448 B2
(45) Date of Patent: Jul. 25, 2023

(54) COMBINATION THERAPIES FOR THE TREATMENT OF CANCER

(71) Applicant: Eisai R&D Management Co., Ltd., Tokyo (JP)

(72) Inventors: Xingfeng Bao, Concord, MA (US); Diana Albu, Windham, NH (US); Mary Woodall-Jappe, Ipswich, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 78 days.

(21) Appl. No.: 17/528,510

(22) Filed: Nov. 17, 2021

(65) Prior Publication Data
US 2022/0071959 A1 Mar. 10, 2022

Related U.S. Application Data

(62) Division of application No. 15/312,980, filed as application No. PCT/US2015/031931 on May 21, 2015, now abandoned.

(60) Provisional application No. 62/002,366, filed on May 23, 2014, provisional application No. 62/150,004, filed on Apr. 20, 2015.

(51) Int. Cl.
| | | |
|---|---|---|
| A61K 31/415 | (2006.01) | |
| A61K 31/7068 | (2006.01) | |
| C07K 16/28 | (2006.01) | |
| A61K 39/00 | (2006.01) | |

(52) U.S. Cl.
CPC ........ A61K 31/415 (2013.01); A61K 31/7068 (2013.01); A61K 39/00 (2013.01); C07K 16/2818 (2013.01); C07K 16/2827 (2013.01); A61K 2039/505 (2013.01); A61K 2300/00 (2013.01)

(58) Field of Classification Search
CPC .. A61K 31/415; A61K 31/7068; A61K 39/00; A61K 2039/505; A61K 2300/00; C07K 16/2818; C07K 16/2827
See application file for complete search history.

(56) References Cited

U.S. PATENT DOCUMENTS

| | | | |
|---|---|---|---|
| 7,029,674 B2 | 4/2006 | Carreno et al. | |
| 7,488,802 B2 | 2/2009 | Collins et al. | |
| 7,521,051 B2 | 4/2009 | Collins et al. | |
| 8,008,449 B2 | 8/2011 | Korman et al. | |
| 8,217,149 B2 | 7/2012 | Irving et al. | |
| 8,293,917 B2 | 10/2012 | Cook et al. | |
| 8,354,509 B2 | 1/2013 | Carven et al. | |
| 8,383,796 B2 | 2/2013 | Korman et al. | |
| 8,552,154 B2 | 10/2013 | Freeman et al. | |
| 8,617,546 B2 | 12/2013 | Kang et al. | |
| 8,685,394 B2 | 4/2014 | Jure-Kunkel | |
| 8,686,018 B2 | 4/2014 | Spyvee et al. | |
| 8,709,417 B2 | 4/2014 | Allison et al. | |
| 8,921,391 B2 | 12/2014 | Take et al. | |
| 9,000,024 B2 | 4/2015 | Spyvee et al. | |
| 2012/0088723 A1 | 4/2012 | Take et al. | |
| 2013/0237578 A1 | 9/2013 | Spyvee et al. | |
| 2014/0155452 A1 | 6/2014 | Spyvee et al. | |
| 2017/0182003 A1 | 6/2017 | Bao et al. | |

FOREIGN PATENT DOCUMENTS

| | | | | |
|---|---|---|---|---|
| CN | 102421429 A | 4/2012 | | |
| CN | 103097358 A | 5/2013 | | |
| EP | 2422779 A1 | 2/2012 | | |
| KR | 20120096402 A | 8/2012 | | |
| KR | 20130099008 A | 9/2013 | | |
| WO | 2010123049 A1 | 10/2010 | | |
| WO | 2012039972 A1 | 3/2012 | | |
| WO | WO-2012039972 A1 | * | 3/2012 | ........... A61K 31/415 |
| WO | 2013090552 A1 | 6/2013 | | |

OTHER PUBLICATIONS

Second Office Action from The State Intellectual Property Office of China dated Nov. 8, 2021 for CN 201910572217.2, with English Translation.
Office Action (Notice of Final Rejection) dated Oct. 21, 2022, by the Korean Patent Office in corresponding Korean Patent Application No. 10-2016-7035808, and an English Translation of the Office Action. (17 pages).
Liu et al. (Year: 2012).
Lei et al. (Year: 2013).
First Office Action from The State Intellectual Property Office of China dated Jun. 26, 2018 for CN 201580039416.7 with English Translation.
International Search Report (PCT/ISA/210) dated Aug. 3, 2015, by the European Patent Office as the International Searching Authority for International Application No. PCT/US2015/031931.
Japanese Office Action dated May 15, 2019, issued for JP 2016-568918, and English translation thereof.
Notice of Reasons for Rejection issued in corresponding Japanese Patent Application No. 2020-096807 dated Jun. 25, 2021, and English Translation.
Office Action (Decision of Rejection) dated Mar. 3, 2020, by the Japanese Patent Office in corresponding Japanese Patent Application No. 2016-568918 and an English Translation of the Office Action. (7 pages).
Written Opinion (PCT/ISA/237) dated Aug. 3, 2015, by the European Patent Office as the International Searching Authority for International Application No. PCT/US2015/031931.

(Continued)

*Primary Examiner* — Jeffrey S Lundgren
*Assistant Examiner* — Ibrahim D Bori
(74) *Attorney, Agent, or Firm* — Buchanan Ingersoll & Rooney PC

(57) ABSTRACT

The present invention provides methods and compositions for treating cancer by administering an EP4 antagonist in combination with radiation therapy, antibody therapy and/or anti-metabolite chemotherapy.

22 Claims, 11 Drawing Sheets

(56) References Cited

OTHER PUBLICATIONS

Albu, Diana I., et al., E7046, an Antagonist of PGE2 Receptor type-4, Induces an Effective Anti-tumor Immune Response in Mice by Attenuating Intratumoral MDSCs and TAMs, Abstract #275, AACR 106th Annual Meeting 2015, Philadelphia, PA, Apr. 18-22, 2015.
Albu, Diana I., et al., Pharmacological Profile of the PGE2 EP4 Receptor Antagonist E7046, Abstract #B198, AACR-NCI-EORTC International Conference: Molecular Targets and Cancer Therapeutics, Boston, MA, Nov. 5-9, 2015.
Albu, Diana I., et al., Preclinical Immune Anti-tumor Activity of Myeloid-Targeting E7046 and Treg-Depleting E7777, Abstract #B034, CRI-GMT-EATI-AACR Inaugural International Cancer Immunotherapy Conference: Translating Science into Survival, New York, NY, Sep. 16-19, 2015.
Bao, Xingfeng, et al., Combination of EP4 Antagonist and Immune Checkpoint Inhibitors Promotes Effector Cytotoxic T cells in Preclinical Tumor Models, Poster #367, Society for Immunotherapy of Cancer (SITC) Conference, National Harbor, MD, Nov. 4-8, 2015.
Blanquicett et al., "Antitumor Efficacy of Capecitabine and Celecoxib in Irradiated and Lead-Shielded, Contralateral Human BxPC-3 Pancreatic Cancer Xenografts: Clinical Implications of Abscopal Effects", Clin Cancer Res, Dec. 15, 2005, 11 (24), pp. 8773-8781.
Chen, et al., "A novel antagonist of the prostaglandin E2 EP4 receptor inhibits Th1 differentiation and Th17 expansion and is orally active in arthritis models", British J. Pharmacol., 2010, pp. 292-310, vol. 160.
Fulton, A. M., et al., "Targeting prostaglandin E EP receptors to inhibit metastasis", Cancer Research, Oct. 2006, vol. 66, No. 20, pp. 9794-9797.
Jure-Kunkel, M., et al., "Synergy between chemotherapeutic agents and CTLA-4 blockade in preclinical tumor models", Cancer Immunology, Immunotherapy, 2013, vol. 62, No. 9, pp. 1533-1545.
Park, W., et al., "Antitumor enhancement of celecoxib, a selective Cyclooxygenase-2 inhibitor, in a Lewis lung carcinoma expressing Cyclooxygenase-2", Journal of Experimental & Clinical Cancer Research, Nov. 2008, 27:66, pp. 1-9.
Rahman, M., et al., "Inhibition of COX-2 in colon cancer modulates tumor growth and MDR-1 expression to enhance tumor regression in therapy-refractory cancers in vivo", Neoplasia, Jul. 2012, vol. 14, No. 7, pp. 624-633.
Tamada, Koji, "Immune checkpoint blockade therapy", Experimental Medicine, 2013, vol. 31, No. 12 (extra edition), p. 1952-1957.
Terada, et al., "Identification of EP4 as a Potential Target for the Treatment of Castration-Resistant Prostate Cancer Using a Novel Xenograft Model", Cancer Res., Feb. 2010, pp. 1606-1615, vol. 70, No. 4.
Vukicevic, et al., "A Maladaptive Role for EP4 Receptors in Mouse Mesangial Cells", Kidney international, 2006 vol. 70, 2006, pp. 1099-1106.
Waldner, "Community-Acquired Bacterial Meningitis in Adults: Categorization of Causes and Timing of Death", Eur. J .Clinical Investigation, vol. 33, 2003, pp. 969-975.
Whiteside, "Inhibiting the Inhibitors: Evaluating Agents Targeting Cancer Immunosuppression", Expert Opinion in Biological Therapy, Jul. 2010, pp. 1019-1035, vol. 10, No. 7.
Xu, G., et al., "Enhancing effects of celeroxib on the growth inhibition of pancreatic carcinoma by gemcitabine treatment", Natl Med J China, Apr. 13, 2005, vol. 85, No. 14, pp. 986-991.
Yang, et al., "Host and Direct Antitumor Effects and Profound Reduction in Tumor Metastasis with Selective EP4 Receptor Antagonism", Cancer Res., Oct. 2006, pp. 9665-9672, vol. 66, No. 19.
Yusup, G., et al., "A COX-2 inhibitor enhances the antitumor effects of chemotherapy and radiotherapy for esophageal squamous cell carcinoma", International Journal of Oncology, Apr. 2014, vol. 44, No. 4, pp. 1146-1152.
Zhang, D. Q., et al., "Increase of cyclooxygenase-2 inhibition with celecoxib combined with 5-FU enhances tumor cell apoptosis and antitumor efficacy in a subcutaneous implantation tumor model of human colon cancer", World Journal of Surgical Oncology, 2013, vol. 11:16, pp. 1-8.

* cited by examiner

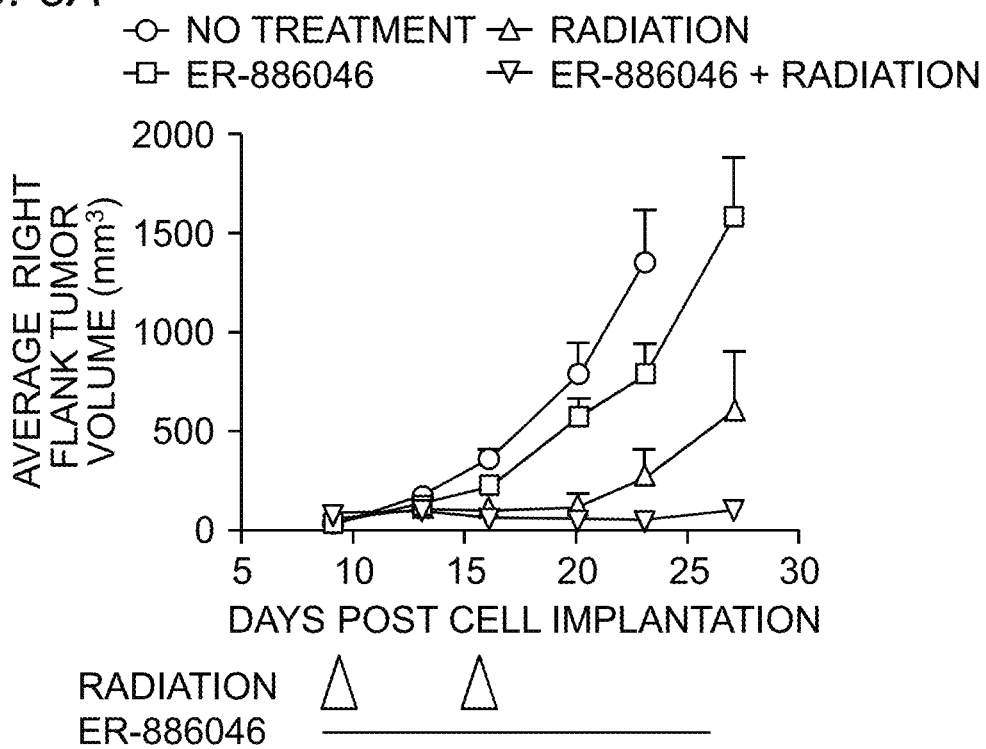
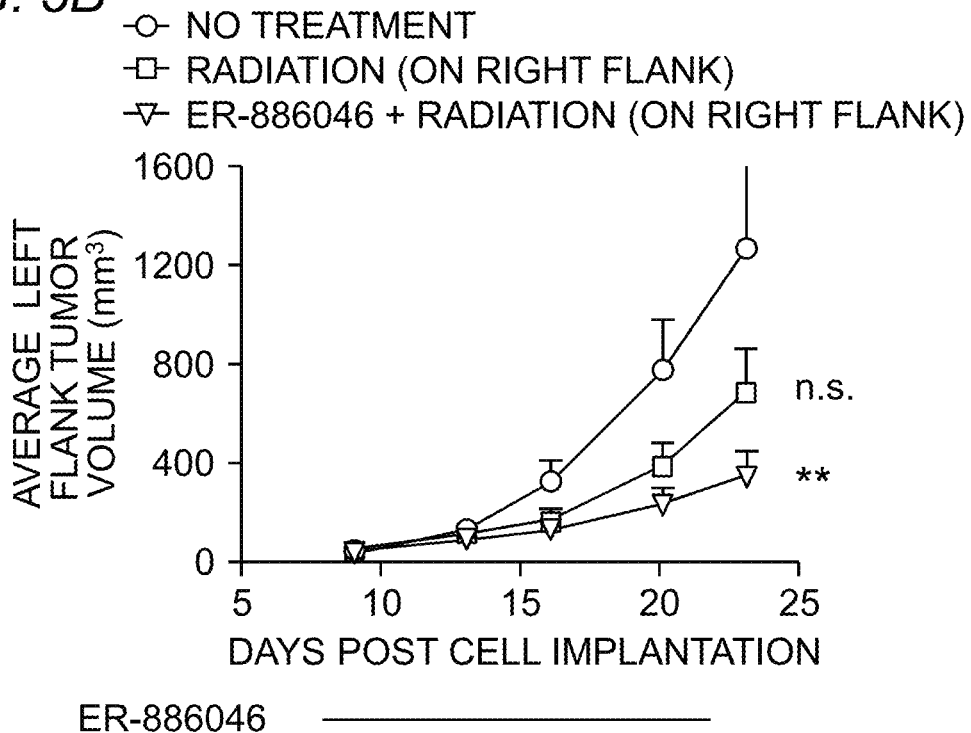

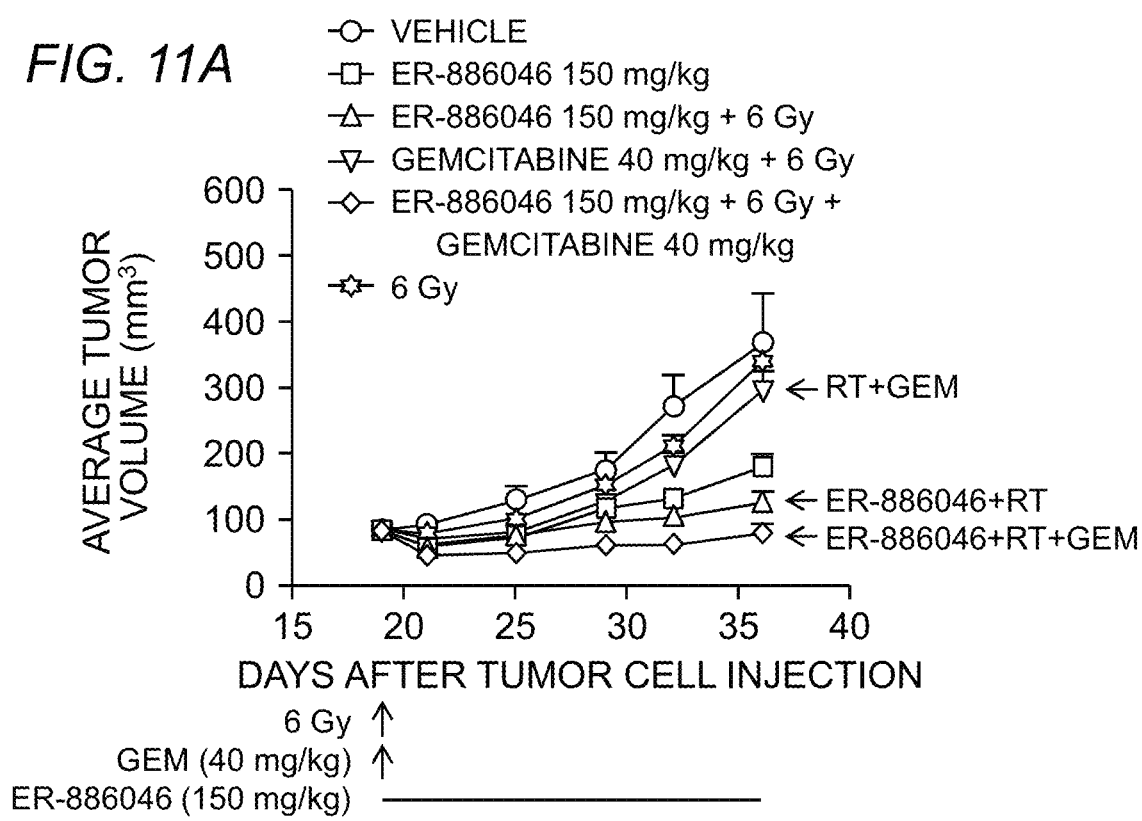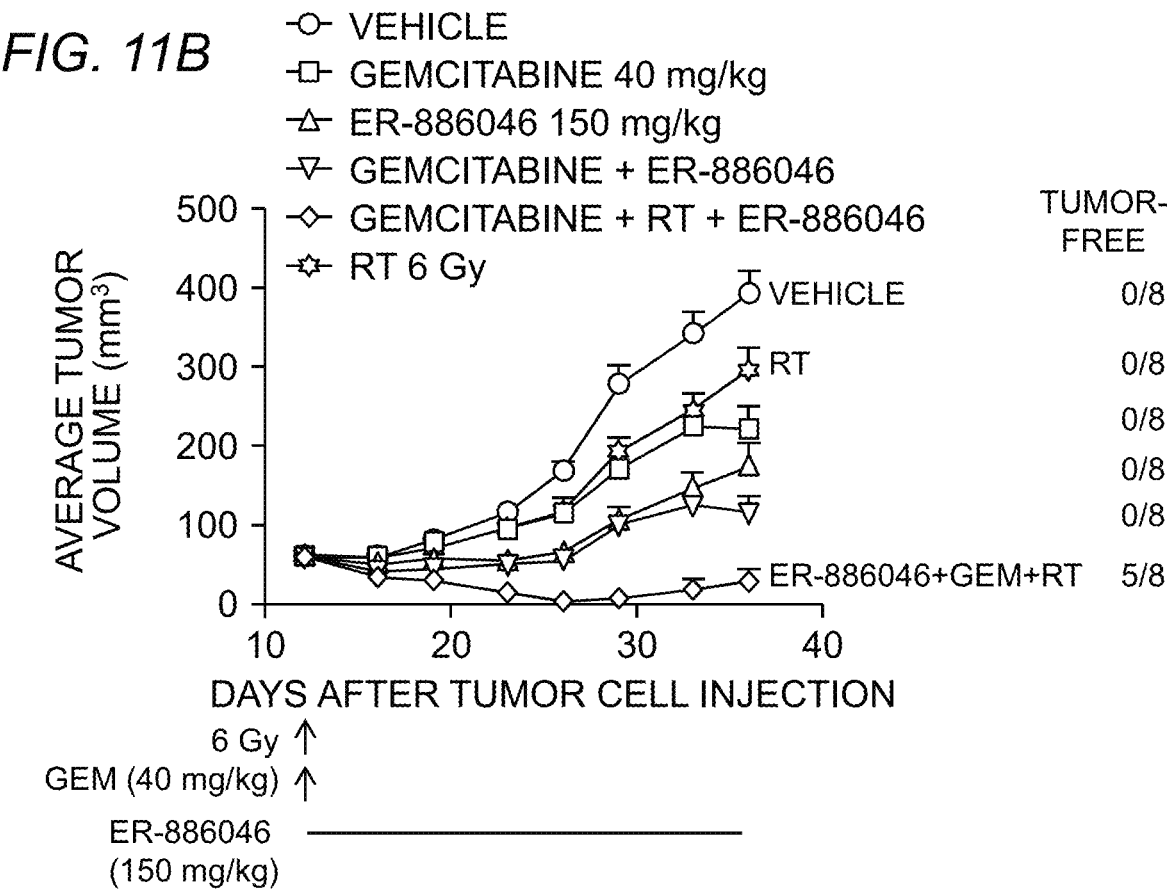

COMBINATION THERAPIES FOR THE TREATMENT OF CANCER

CROSS REFERENCE TO RELATED APPLICATIONS

This application is a divisional application claiming benefit of priority of U.S. patent application Ser. No. 15/312,980, having a 35 U.S.C. § 371(c) date of Nov. 21, 2016 as the United States national stage of PCT International Application No. PCT/US2015/031931, filed on May 21, 2015, which claimed benefit of U.S. Provisional Patent Application No. 62/002,366, filed on May 23, 2014, and U.S. Provisional Patent Application No. 62/150,004, filed on Apr. 20, 2015, all of which are incorporated by reference herein.

BACKGROUND

Blocking of prostaglandin E2 (PGE2) signaling through the interaction of PGE2 with the prostaglandin E receptor 4 (EP4) by antagonists has been shown to be effective in reducing inflammation (Chen et al. (2010) *British J. Pharmacol.* 160, 292-310). PGE2 has also been implicated as an important constituent in the immunosuppressive environment created by many solid tumors (Whiteside (2010) *Expert Opinion in Biological Therapy.* 2010. 10, 1019-1035), and inhibition of EP4 signaling by antagonists were shown to reduce tumor growth (Terada et al. (2010) *Cancer Res.* 70, 1606-1615) and tumor metastasis in tumor animal models (Yang et al. (2006) *Cancer Res.* 66, 9665-9672).

Even with the most advanced cancer therapies, there continues to be a medical need for more effective treatments for solid cancers, particularly cancer that has metastasized.

SUMMARY

The anti-tumor activities of various combinations of an EP4 antagonist with: radiation; antibodies to cytotoxic t-lymphocyte antigen 4 (anti-CTLA4); antibodies to programmed death ligand 1 (anti-PDL1); antibodies to programmed cell death protein 1 (anti-PD1); and anti-metabolites have been examined. The results from this examination have indicated improved and/or synergistic anti-tumor activities by the combination of the EP4 antagonist with the other therapies as compared to single agent treatment alone, and in some embodiments this may result in a memory immune response against the tumor, even as against a different cancer.

Thus, in one aspect of the invention, provided is a method of treating cancer in a subject in need thereof comprising administering an EP4 antagonist in combination with a therapy selected from the group consisting of radiation therapy, antibody therapy and anti-metabolite chemotherapy. In a more particular aspect of the invention, the antibody therapy is selected from the group consisting of CTLA4 antibody therapy, PDL1 antibody therapy, and PD1 antibody therapy. In some embodiments, the cancer is metastatic cancer.

In another aspect of the invention, provided is a method of generating a memory immune response in a subject in need thereof comprising administering an amount of an EP4 antagonist in combination with a therapy selected from the group consisting of radiation therapy, antibody therapy and anti-metabolite chemotherapy. In another more particular aspect of the invention, the antibody therapy is selected from the group consisting of CTLA4 antibody therapy, PDL1 antibody therapy and PD1 antibody therapy.

In yet another aspect of the invention, the cancer treated is selected from the group consisting of breast cancers, cervical cancers, colorectal cancers, endometrial cancers, glioblastomas, head and neck cancers, kidney cancers, liver cancers, lung cancers, medulloblastomas, ovarian cancers, pancreatic cancers, prostate cancers, skin cancers and urinary tract cancers.

In more particular aspects of the invention, provided are methods of treating cancer and/or generating a memory immune response comprising administering a compound of Formula (I):

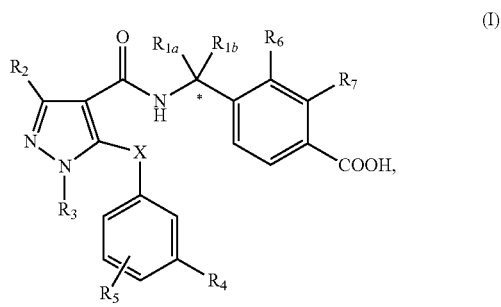

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, methyl, fluoromethyl, methoxy, or fluoromethoxy;
$R_5$ is hydrogen, halo, methyl, fluoromethyl, methoxy, or fluoromethoxy;
$R_6$ is hydrogen, halo, methyl, or methoxy;
$R_7$ is hydrogen, halo, methyl, or methoxy; and
X is oxygen;
or a pharmaceutically acceptable salt thereof,
in combination with radiation therapy; in combination with anti-CTLA4 therapy; in combination with anti-PDL1 therapy; in combination with anti-PD1 therapy; and/or in combination with anti-metabolite chemotherapy.

Further provided is the use of a combination of an EP4 antagonist and a therapy selected from the group consisting of radiation therapy, antibody therapy and/or anti-metabolite chemotherapy for treating cancer and/or generating a memory immune response as disclosed herein.

Also provided is the use of an EP4 antagonist in the preparation of a medicament for a combination therapy with a therapy selected from the group consisting of radiation therapy, antibody therapy and/or anti-metabolite chemotherapy for treating cancer and/or generating a memory immune response as disclosed herein.

BRIEF DESCRIPTION OF THE DRAWINGS

FIG. 5A to FIG. 5B. Anti-tumor effect of ER-886046/radiation in a bilateral tumor model. Two similar-sized CT-26 tumors were grown in a host by injecting CT26 cells subcutaneously on both right and left flanks of BalB/c mice. Radiation was applied to the right flank tumor on both day 9 and day 13 as indicated by arrows in panel A. ER-886046 was administered daily po to the animals at a dose of 150 mg/kg as indicated by the bars. ER-886046 was dosed to animals from day 9 to day 27. Panel shown in FIG. 5A) Average size of the right flank tumor that received radiation and ER-886046. Panel shown in FIG. 5B) Average size of the left flank tumor that received no radiation (radiation administered only to the right flank tumor). Note that the combination of radiation/ER-886046 administered to the right flank tumor significantly slowed the growth of the left flank tumor of the same origin, which did not receive radiation treatment, indicating an abscopic effect. **, p<0.01; ns, not significant; student t-test.

FIG. 11A to FIG. 11B. Additional experiments with combination therapy of ER-886046 and anti-metabolite chemotherapy with radiation compared to anti-metabolite chemotherapy with radiation alone. Panel shown in FIG. 11A) Gemcitabine and RT dosing: a single 40 mg/kg dose of gemcitabine and a single 6 Gy dose of RT, was administered on day 19 post tumor cell injection. ER-8806046 was administered daily in an amount of 150 mg/kg from day 19 post tumor cell injection until the end of the study. Panel shown in FIG. 11B) Gemcitabine and RT dosing: a single 40 mg/kg dose of gemcitabine and a single 6 Gy dose of RT, was administered on day 12 post tumor cell injection. ER-8806046 was administered daily in an amount of 150 mg/kg from day 12 post tumor cell injection until the end of the study. Average tumor sizes of mouse pancreatic PAN02 tumor-bearing mice that received vehicles, ER-886046, gemcitabine (gem) plus radiation (RT), ER-886046 plus RT, or ER-886046 plus gemcitabine and RT at indicated dosages and schedules. A and B represent each independent study. N=8-10 per group. NS, not significant; *, p<0.05; , p<0.01; *, p<0.001; and ****, p<0.0001, two-way ANOVA test.

DETAILED DESCRIPTION OF EMBODIMENTS

Figure 1A:
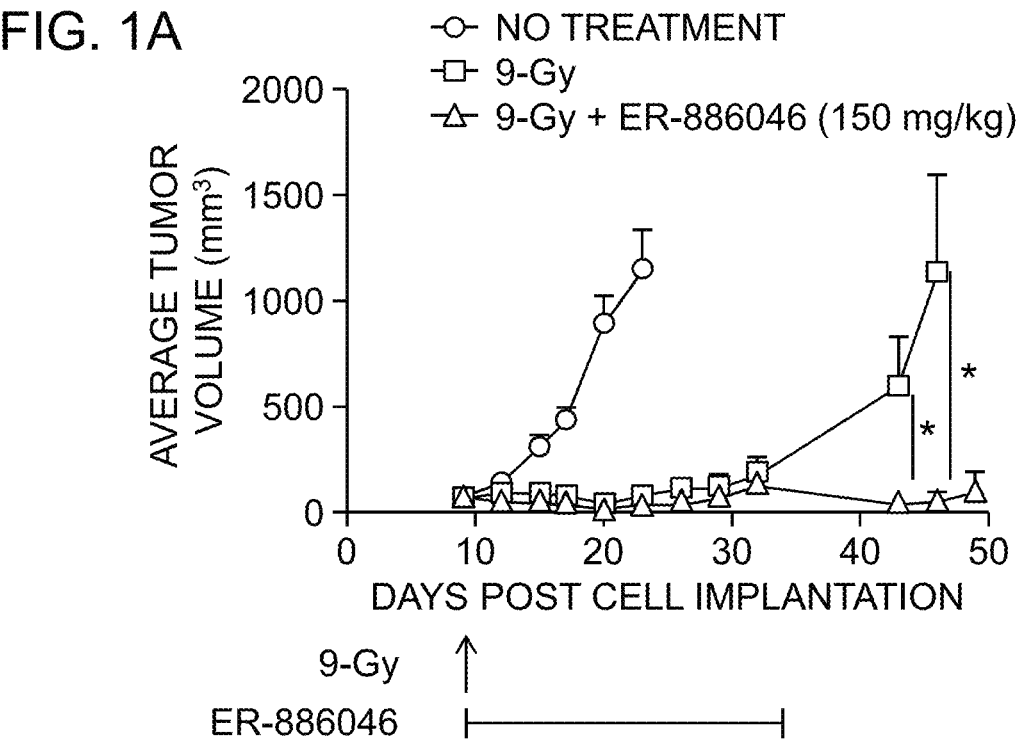
FIG. 1A to FIG. 1B. Significantly improved anti-tumor growth activity of radiation/ER-886046 combination therapy compared with radiation alone. Panel shown in FIG. 1A) Average tumor sizes of the CT26 tumor-bearing mice that received 9 Gy radiation+ER-886046, 9 Gy radiation alone, or vehicle alone. Panel shown in FIG. 1B) Average animal body weight of the CT-26 tumor-bearing mice. Radiation treatment: 9 Gy single dose on day 9; ER-886046 dosing: 150 mg/kg, oral (po) administration daily from day 9 to day 32. Administration of radiation and ER-886046 to the tumor-bearing mice is indicated by the arrows and bars, respectively. N=10-12 per group. *, p<0.05, student t-test.

"EP4 antagonist" refers to a compound which inhibits or blocks the cellular signaling triggered by the interaction of PGE2 with the EP4 receptor. Examples of EP4 antagonists include, but are not limited to, ER-819762, MK-2894, MF 498, ONO-AE3-208, evatanepag, ONO-AE2-227, CJ-042794, EP4A, BGC201531, CJ-023423, ONO-AE3-240, GW 627368 and AH23848, such as are listed in the IUPHAR database as antagonists of the EP4 receptor. Further examples include, but are not limited to, compounds of Formula (I) as taught herein, including ER-885290, ER-885740, ER-885741, ER-886045, ER-886046 (E7046), ER-886074, ER-885290, ER-885740 and ER-885741, which are described in WO 2012/039972.

"CTLA4 antibody" or "anti-CTLA4" refers to an antibody or antibodies directed towards cytotoxic t-lymphocyte antigen 4 (CTLA4). Exemplary antibodies include, but are not limited to, antibodies that are CTLA4 antagonists or the CTLA4 antibodies as set forth in U.S. Pat. Nos. 8,685,394 and 8,709,417. Some embodiments of the antibody include MDX-010 (ipilimumab, Bristol-Myers Squibb) and CP-675,206 (tremelimumab, Pfizer). In a particular embodiment, the antibody is ipilimumab.

"PDL1 antibody" or "anti-PDL1" refers to an antibody directed towards programmed death ligand 1 (PDL1). Exemplary antibodies include, but are not limited to, the antibodies set forth in U.S. Pat. Nos. 8,217,149, 8,383,796, 8,552,154 and 8,617,546. In a particular embodiment, the antibody is MPDL3280A (Roche).

"PD1 antibody" or "anti-PD1" refers to an antibody directed towards programmed death protein 1 (PD1). Exemplary antibodies include, but are not limited to, the antibodies set forth in U.S. Pat. Nos. 7,029,674, 7,488,802, 7,521,051, 8,008,449, 8,354,509, 8,617,546 and 8,709,417.

Particular embodiments of the antibody include MDX-1106 (nivolumab, Bristol-Myers Squibb), labrolizumab (Merck), and pembrolizumab (KEYTRUDA®, Merck).

"Treatment," "treat," and "treating" refer to alleviating, inhibiting and/or reversing the progress of a cancer in a subject in need thereof. The term "treating" is inclusive of any indicia of success in the treatment or amelioration of the cancer, including any objective or subjective parameter such as abatement; remission; diminishing of symptoms or making the injury, pathology or condition more tolerable to the subject; delaying or slowing in the rate of progression, etc.

Measurement of the treatment or amelioration may be based on, e.g., the results of a physical examination, a pathological test and/or a diagnostic test as known in the art.

Treating may also refer to reducing the incidence or onset of a cancer, or a recurrence thereof (such as a lengthening in time of remission), as compared to that which would occur in the absence of the measure taken.

"Effective amount" or "treatment-effective amount" refers to an amount that is effective for treating a cancer as noted through clinical testing and evaluation, patient observation, and/or the like. An "effective amount" can further designate an amount that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition. An "effective amount" can further refer to a therapeutically effective amount.

"Subject" as used herein refers a mammalian subject, and particularly a human subject, including a male or female subject, and including a neonatal, infant, juvenile, adolescent, adult or geriatric subject, and further is inclusive of various races and ethnicities.

As used herein, the term "a pharmaceutically acceptable salt" refers to a relatively non-toxic, inorganic or organic acid salt of a compound of the invention. These salts may be prepared in situ during the final isolation and purification of the compounds or by reacting the purified compound in its free form separately with a suitable organic or inorganic acid and isolating the salt thus formed. Representative acid salts include, but are not limited to, acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts. In one embodiment, the pharmaceutically acceptable salt is a hydrochloride/chloride salt.

"Cancer" as used herein may include cancers that are the result of genetically inherited mutations. Examples of such cancers include, but are not limited to, breast cancers, cancers which can be related to Li-Fraumeni syndrome, for example, childhood sarcomas, leukemias and brain cancers, cancers which can be related to Lynch syndrome, for example, colon cancers, bile duct cancers, brain cancers, endometrial cancers, kidney cancers, ovarian cancers, pancreatic cancers, small intestinal cancers, stomach cancers and ureter cancers, lung cancers, melanomas, prostate cancers, retinoblastomas, thyroid cancers and uterine cancers.

Moreover, cancer can be the result of acquired mutations, for example, mutations resulting from diet, environment and/or lifestyle, or somatic mutations. Examples of such cancers may include, but are not limited to, adrenal cancer, adrenal cortex cancer, bladder cancer, brain cancer, primary brain cancer, glioma, glioblastoma, breast cancer, cervical cancer, colon cancer (non-limiting examples include colorectal carcinomas such as colon adenocarcinoma and colon adoma), endometrial cancer, epidermal cancer, esophageal cancer, gall bladder cancer, genitourinary cancer, head or neck cancer, kidney cancer, liver cancer, lung cancer (non-limiting examples include adenocarcinoma, small cell lung cancer and non-small cell lung cancer), lymphomas (non-limiting examples include B-cell lymphoma, T-cell lymphoma, Hodgkin's lymphoma, non-Hodgkin's lymphoma), melanoma, malignant melanoma, malignant carcinoid carcinoma, malignant pancreatic insulinoma, myeloma, multiple myeloma, ovarian cancer, pancreatic cancer (such as exocrine pancreatic carcinoma), prostate cancer, renal cell cancer, skin cancer, such as, in addition to others previously mentioned, squamous cell carcinoma, stomach cancer, testicular cancer, thyroid cancer, thyroid follicular cancer, Wilms' tumor, choriocarcinoma, mycosis fungoides, malignant hypercalcemia, cervical hyperplasia, leukemia, acute lymphocytic leukemia, chronic lymphocytic leukemia, hairy cell lymphoma, Burkett's lymphoma, acute myelogenous leukemia, chronic myelogenous leukemia, myelodysplastic syndrome, promyelocytic leukemia, chronic granulocytic leukemia, acute granulocytic leukemia, fibrosarcoma, habdomyosarcoma, astrocytoma, neuroblastoma, rhabdomyosarcoma, schwannoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, seminoma, teratocarcinoma, osteosarcoma, xenoderoma pigmentoum, keratoctanthoma and retinoblastoma.

"Metastatic cancer" refers to a cancer in which cancerous cells from an organ or body part has spread (through "metastasis") to another, non-adjacent organ or body part. The cancer at the non-adjacent organ or body part ("secondary tumor" or "metastatic tumor") includes cancerous cells originating from the organ or body part from which the cancer or cancerous cells has spread. Sites in which the secondary tumor may occur include, but are not limited to, lymph nodes, the lungs, liver, brain and/or bones.

In some embodiments of the invention, the EP4 antagonist used in the methods and compositions taught herein is a compound of Formula (I):

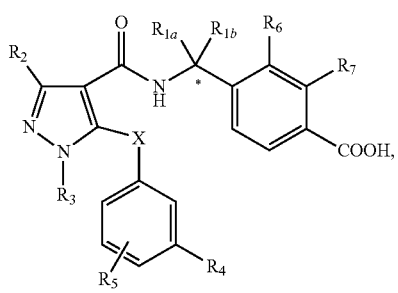

wherein:
one of $R_{1a}$ and $R_{1b}$ is hydrogen, and the other is methyl; or $R_{1a}$ and $R_{1b}$ are taken together to form a cyclopropyl ring;
$R_2$ is methyl or fluoromethyl;
$R_3$ is methyl;
$R_4$ is hydrogen, halo, methyl, fluoromethyl, methoxy, or fluoromethoxy;
$R_5$ is hydrogen, halo, methyl, fluoromethyl, methoxy, or fluoromethoxy;
$R_6$ is hydrogen, halo, methyl, or methoxy;
$R_7$ is hydrogen, halo, methyl, or methoxy; and
X is oxygen;
or a pharmaceutically acceptable salt thereof.

Compounds of Formula (I) are known and their synthesis described in WO 2012/039972, the disclosures of which are incorporated by reference herein.

Unless indicated otherwise, nomenclature used to describe chemical groups or moieties as used herein follow the convention where, reading the name from left to right, the point of attachment to the rest of the molecule is at the right-hand side of the name. For example, the group "methoxy" is attached to the rest of the molecule at the oxygen end. Further examples include methoxyethyl, where the point of attachment is at the ethyl end.

"Fluoromethyl" as used herein refers to a methyl group substituted with one or more fluoro atoms (e.g., monofluoromethyl, difluoromethyl, trifluoromethyl).

"Fluoromethoxy" as used herein, refers to an fluoromethyl group, as previously defined, attached to the principal carbon chain through an oxygen atom.

In some embodiments of Formula (I), one of $R_{1a}$ and $R_{1b}$ is hydrogen, and the other is methyl; $R_2$ is methyl, difluoromethyl, or trifluoromethyl; $R_3$ is methyl; $R_4$ is chloro, fluoro, trifluoromethyl, difluoromethyl, methyl, methoxy, difluoromethoxy, or trifluoromethoxy; $R_5$ is hydrogen, chloro, fluoro, methyl, or methoxy; and $R_6$ and $R_7$ are hydrogen. In some embodiments, $R_5$ is hydrogen. In some embodiments, $R_4$ is selected from chloro, trifluoromethyl, difluoromethyl, difluoromethoxy, and trifluoromethoxy.

In some embodiments of Formula (I), $R_{1a}$ and $R_{1b}$ are taken together to form a cyclopropyl ring; $R_2$ is methyl, trifluoromethyl, or difluoromethyl; $R_3$ is methyl; $R_4$ is trifluoromethyl, difluoromethyl, chloro, or fluoro; and $R_6$ and $R_7$ are hydrogen.

In some embodiments, the compound of Formula (I) is:

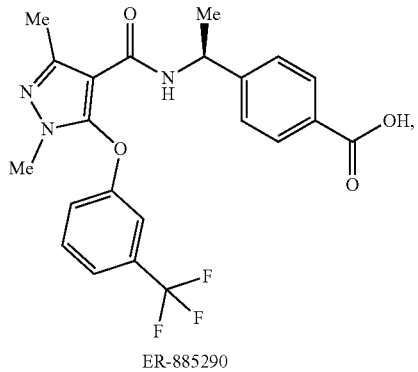

ER-885290

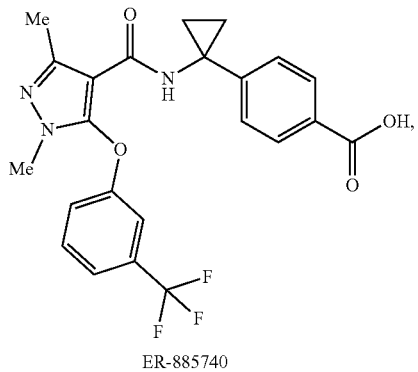

ER-885740

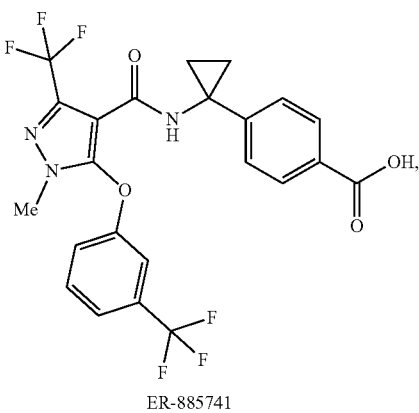

ER-885741

-continued

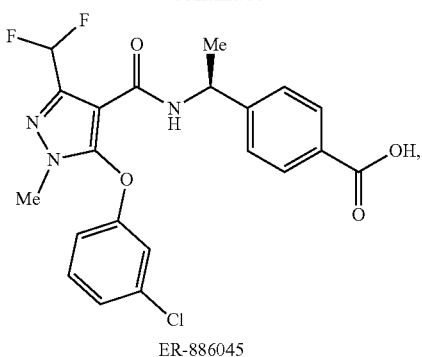

ER-886045

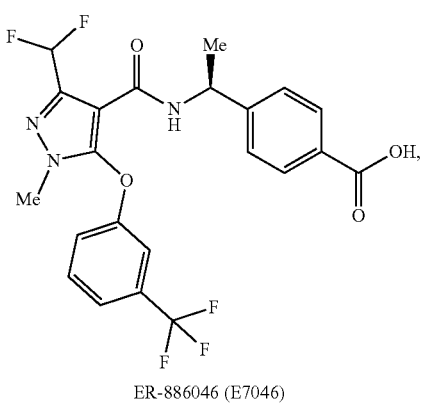 [SMILES: C[C@H](NC(=O)c1c(C(F)F)nn(C)c1Oc1cccc(C(F)(F)F)c1)c1ccc(C(=O)O)cc1]

ER-886046 (E7046)

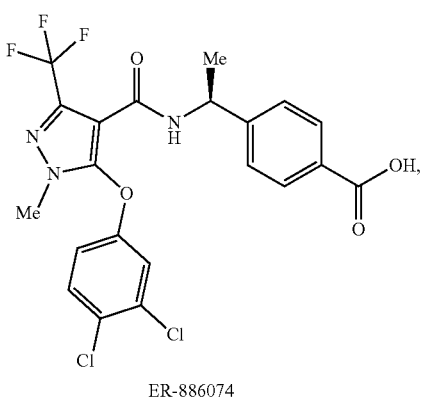

ER-886074

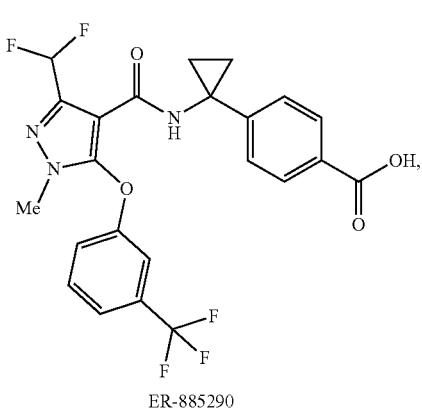

ER-885290

-continued

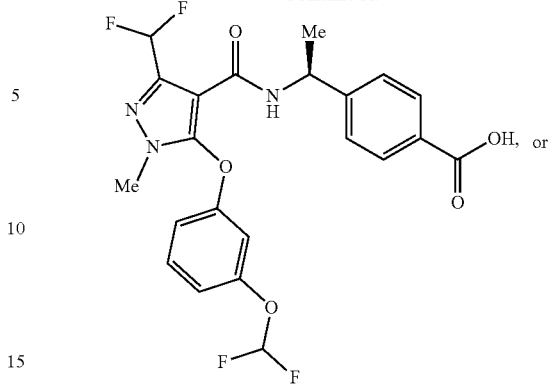

ER-885740

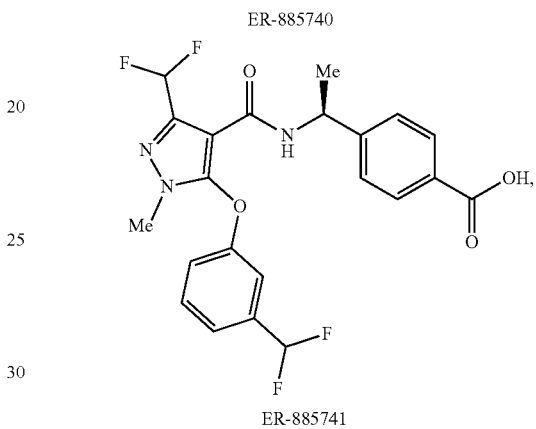

ER-885741 or a pharmaceutically acceptable salt thereof.

In a particular embodiment, the compound of Formula (I) is:

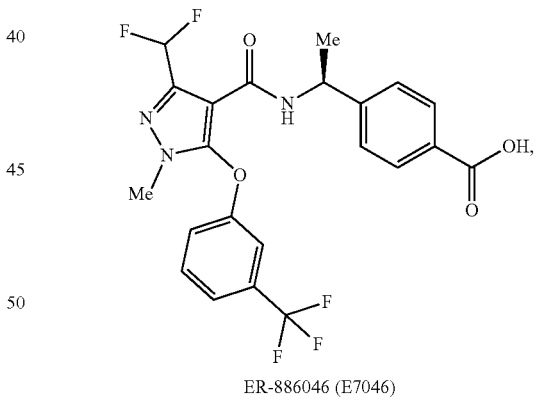

ER-886046 (E7046)

or a pharmaceutically acceptable salt thereof.

In some embodiments of the present invention, provided is a method of inhibiting tumor growth or treating cancer wherein an EP4 antagonist is administered in combination with an additional therapy or agent useful for inhibiting tumor growth and/or treating cancer, i.e., a combination therapy.

As used herein, the administration of two or more agents/therapies (inclusive of EP4 antagonists, radiation therapy, antibody therapy, anti-metabolite chemotherapy, or any combination thereof) "in combination" means that the therapies are administered closely enough in time that the administration of or presence of one alters the biological effects of the other. The therapies may be administered simultaneously (concurrently) or sequentially.

Simultaneous administration may be carried out, e.g., by mixing two or more agents prior to administration, or by administering the agent/therapy at the same point in time but at different anatomic sites or using different routes of administration, or administered at times sufficiently close that the results observed are indistinguishable from those achieved when the agents/therapies are administered at the same point in time. For example, simultaneous administration of one or more agents with radiation may be carried out by administering the agent(s) at the same point in time as the radiation is applied, or at times sufficiently close that the results observed are indistinguishable from those achieved when the agent(s) and radiation are administered at the same point in time.

Sequential administration may be carried out by administering the agents/therapies at different points in time, e.g., administering an agent/therapy at some point in time prior to or after administration of one or more other agents/therapies, such that the administration of the agents/therapies in combination enhances the therapeutic effect of cancer treatment. In some embodiments, an EP4 antagonist is administered at some point in time prior to the initial administration of radiation therapy, antibody therapy and/or anti-metabolite chemotherapy.

Alternatively, the radiation therapy, antibody therapy and/or anti-metabolite chemotherapy may be administered at some point in time prior to the administration of the EP4 antagonist, and optionally, administered again at some point in time after the administration of the EP4 antagonist.

In some embodiments, administration of the EP4 antagonist in combination with radiation therapy, antibody therapy and/or anti-metabolite chemotherapy results in an enhancement of said radiation therapy, antibody therapy and/or anti-metabolite chemotherapy such that, for example, a smaller dosage of the radiation, antibody therapy and/or anti-metabolite chemotherapy may be effective for treatment.

In some embodiments of the invention, the treatment of cancer may comprise an abscopal effect and/or provide a memory immune response.

An "abscopal" effect is a phenomenon in the treatment of a metastatic cancer in which localized treatment of a particular tumor or cancer with, for example, radiation therapy, results in the shrinking and disappearance of non-localized disease, tumors or cancer, such as those resulting from metastasis that are distant from the site of localized treatment, thus leading to the disappearance of disease, tumors or cancer throughout the subject or patient. An abscopic effect differs from effects that may occur on tissues adjacent to the localized treatment, such as, for example, bystander effects that may result from radiation therapy.

A "memory immune response" results when the provided treatment for cancer facilitates the adaptation of the immune system and the immune response of the subject or patient in its ability to slow, reduce or prevent the return or the recurrence, e.g., lengthening the time of remission, of the disease, tumor or cancer being treated in the subject or patient. In some embodiments, the memory immune response may slow, reduce or prevent the development of tumors or cancers that are different than the cancer being treated, e.g., through epitope spreading.

The EP4 antagonist, antibody and/or anti-metabolite as used herein may be formulated for administration in a pharmaceutical carrier in accordance with known techniques. See, for example, Remington, The Science and Practice of Pharmacy (9th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients and/or excipients.

In some embodiments, any of the composition(s), carrier(s), accessory ingredient(s) excipient(s) and/or the formulation(s) of the invention comprise ingredients that are from either natural or non-natural sources. In other embodiments, any component of the composition(s), carrier(s), accessory ingredient(s), excipient(s) and/or the formulation(s) of the invention may be provided in a sterile form. Non-limiting examples of a sterile carrier include endotoxin-free water or pyrogen-free water.

The EP4 antagonist, antibody and/or anti-metabolite can be administered to subjects by any suitable route, including orally (inclusive of administration via the oral cavity and further including administration via an orogastric feeding tube), intraperitoneally, parenterally, by inhalation spray, topically (i.e., both skin and mucosal surfaces, including airway surfaces), transdermally, rectally, nasally (including a nasogastric feeding tube), sublingually, buccally, vaginally or via an implanted reservoir. The term "parenteral" as used herein includes subcutaneous, intramuscular, intradermal, intravenous, intra-articular, intra-synovial, intrasternal, intrathecal, intrahepatic, intralesional and intracranial injection or infusion techniques. In a particular embodiment, the EP4 antagonist, antibody and/or anti-metabolite is administered orally. In another particular embodiment, the EP4 antagonist, antibody and/or anti-metabolite is administered intravenously.

In some embodiments, the amount of the EP4 antagonist, antibody and/or anti-metabolite that may be combined with the excipient materials to produce a composition in a single dosage form will vary depending upon the host treated, and the particular route of administration.

In some embodiments, the EP4 antagonist, antibody and/or or anti-metabolite is provided as part of a sterile composition/formulation comprising the EP4 antagonist, antibody and/or anti-metabolite and an acceptable carrier and/or excipient.

In some embodiments, the EP4 antagonist is administered to the subject in an effective amount. An effective amount is generally 0.01 mg/kg to 500 mg/kg body weight per day. In some embodiments, the pharmaceutically acceptable compositions may be formulated so that a dosage of from 0.01 mg/kg to 200 mg/kg or from 0.01 mg/kg to 100 mg/kg body weight per day of the compound can be administered to a patient receiving these compositions (e.g., based on a 75 kg human, a dosage of from 0.75 mg to 7.5 g or 15 g). In certain embodiments, the compositions of the present invention are formulated to provide a dosage of from 0.01 mg/kg to 70 mg/kg (e.g., based on a 75 kg human, a dosage of from 0.75 mg to 5.25 g).

In some embodiments, the effective dose of the EP4 antagonist is from about 0.5 to about 250 mg/kg, 1 to about 250 mg/kg, from about 2 to about 200 mg/kg, from about 3 to about 120 mg/kg, from about 5 to about 250 mg/kg, from about 10 to about 200 mg/kg, or from about 20 to about 120 mg/kg. In some embodiments, effective dosages include about 0.5 mg/kg, 1 mg/kg, 2 mg/kg, 3 mg/kg, 4 mg/kg, 5 mg/kg, 6 mg/kg, 8 mg/kg, 10 mg/kg, 20 mg/kg, 25 mg/kg, 40 mg/kg, 50 mg/kg, 60 mg/kg, 75 mg/kg, 100 mg/kg, 120 mg/kg, 150 mg/kg, 175 mg/kg, 200 mg/kg, 225 mg/kg, 250 mg/kg, and 300 mg/kg. Dosage forms can be in the form, e.g., of tablets or capsules, and the effective dose may be provided in one or more tablets, capsules or the like, and be provided once a day or throughout the day at intervals, e.g., of 4, 8 or 12 hours. Tablets or capsules, for example, could contain, e.g., 10, 25, 50, 75, 100, 150, 200, 250, 300, 350, 400, 450, 500, 600, 700, 800, 900, 1,000, 1,100, or 1,250 mg of compound. For example, administration to a human subject of the EP4 antagonist in some embodiments may comprise a daily dosage of the EP4 antagonist in the range of 100-1,250, 150-1,000, 200-800, or 250-750 mg, which daily dosage can be administered either once a day in its entirety or fractions of which are administered throughout the day in intervals. Liquid formulations can also be prepared so that any dosage may readily and conveniently be dispensed.

The antibody, e.g., anti-CTLA4, anti-PDL1 or anti-PD1, will generally be mixed, prior to administration, with a non-toxic, pharmaceutically acceptable carrier substance (e.g., normal saline or phosphate-buffered saline), and may be administered using any medically appropriate procedure, for example, including but not limited to, intravenous or intra-arterial administration, and injection into the cerebrospinal fluid. In certain cases, intraperitoneal intradermal, intracavity, intrathecal or direct administration to a tumor or to an artery supplying the tumor may be advantageous.

In some embodiments, the effective dose of the antibody is from about 5 to about 250 mg/kg, from about 10 to about 200 mg/kg, or from about 20 to about 120 mg/kg. In some embodiments, effective dosages include 5 mg/kg, 10 mg/kg, 20 mg/kg, 25 mg/kg, 40 mg/kg, 50 mg/kg, 60 mg/kg, 75 mg/kg, 100 mg/kg, 120 mg/kg, 150 mg/kg, 175 mg/kg, 200 mg/kg, 225 mg/kg, 250 mg/kg, and 300 mg/kg. Dosage forms can be in the form, e.g., of tablets or capsules, and the effective dose may be provided in one or more tablets, capsules or the like, and be provided once a day or throughout the day at intervals, e.g., of 4, 8 or 12 hours. Tablets or capsules, for example, could contain, e.g., 10, 25, 50, 75, 100, 150, 200, 250, 300, 350, 400, 450, 500, 600, 700, 800, 900, or 1,000 mg of antibody. Liquid formulations can also be prepared so that any dosage may readily and conveniently be dispensed.

In some embodiments, the antibody is administered to the subject in an effective amount. An effective amount is generally 0.01 mg/kg to 500 mg/kg body weight per day. In some embodiments, the pharmaceutically acceptable compositions may be formulated so that a dosage of from 0.01 mg/kg to 200 mg/kg or from 0.01 mg/kg to 100 mg/kg body weight per day of the compound can be administered to a patient receiving these compositions (e.g., based on a 75 kg human, a dosage of from 0.75 mg to 7.5 g or 15 g). In certain embodiments, the compositions of the present invention are formulated to provide a dosage of from 0.01 mg/kg to 70 mg/kg (e.g., based on a 75 kg human, a dosage of from 0.75 mg to 5.25 g).

An effective amount of the antibody may be, for example, 0.05 mg/kg, 0.1 mg/kg, 1 mg/kg, 2 mg/kg, 3 mg/kg, 4 mg/kg, 5 mg/kg, 6 mg/kg, 7 mg/kg or 8 mg/kg per dose (e.g., based on a 75 kg human, a dosage of from 3.75 mg to 600 mg).

The dosage of the antibody may be administered once, twice, three times, four times, five times or more per week, once every week, once every two weeks, or even once every three weeks during the course of treatment. The timing of the dosing may be daily, once every two days, once every three days, once every four days, once every five days, weekly, once every two weeks or once every three weeks. Formulations comprising the antibody may be prepared so that any dosage may readily and conveniently be dispensed.

"Radiation therapy" refers to the medical use of ionizing radiation, particularly for the treatment of cancer. Preferably, the medical use of ionizing radiation in the treatment of cancer results in the reduction of and/or killing of cancer cells in the subject.

Radiation therapy may be administered by any manner that would be understood by one of skill in the art. Examples of radiation utilized in radiation therapy include, but are not limited to, photon, ionizing or charged particle radiation, such as X-rays or protons. Examples of radiation therapy include, but are not limited to: external beam radiation therapy or teletherapy; brachytherapy or sealed beam source therapy; and systemic radioisotope therapy or unsealed source radiotherapy.

The dosage of radiation administered may vary depending upon the target cancer or tumor. In some embodiments, dosages of radiation may be 80 grays (Gy), 60 Gy, 40 Gy, 20 Gy, 12 Gy, 10 Gy, 9 Gy, 8 Gy, 7 Gy, 6 Gy, 5 Gy, 4 Gy, 3 Gy, 2 Gy or 1 Gy, including any amount in between those indicated, and/or ranges thereof. In some embodiments, the dosage is 12 Gy, 9 Gy, 6 Gy or 3 Gy. The dosage of radiation may be administered once, twice, three times, four times, five times or more per week, for one, two, three, four or five weeks or more during the course of treatment.

In some embodiments, the anti-metabolite is administered to the subject in an effective amount. An effective amount is generally 0.01 mg/kg to 500 mg/kg body weight per day. In some embodiments, the pharmaceutically acceptable compositions may be formulated so that a dosage of from 0.01 mg/kg to 200 mg/kg or from 0.01 mg/kg to 100 mg/kg body weight can be administered to a patient receiving these compositions (e.g., based on a 75 kg human, a dosage of from 0.75 mg to 7.5 g or 15 g). In certain embodiments, the compositions of the present invention are formulated to provide a dosage of from 0.01 mg/kg to 70 mg/kg (e.g., based on a 75 kg human, a dosage of from 0.75 mg to 5.25 g).

In some embodiments, the effective dose of the anti-metabolite is from about 0.5 to about 250 mg/kg, 1 to about 200 mg/kg, from about 2 to about 175 mg/kg, from about 3 to about 150 mg/kg, from about 5 to about 125 mg/kg, from about 10 to about 100 mg/kg, or from about 20 to about 80 mg/kg. In some embodiments, effective dosages include about 0.5 mg/kg, 1 mg/kg, 2 mg/kg, 3 mg/kg, 4 mg/kg, 5 mg/kg, 6 mg/kg, 8 mg/kg, 10 mg/kg, 20 mg/kg, 25 mg/kg, 40 mg/kg, 50 mg/kg, 60 mg/kg, 75 mg/kg, 100 mg/kg, 120 mg/kg, 150 mg/kg, 175 mg/kg, 200 mg/kg, 225 mg/kg, 250 mg/kg, and 300 mg/kg. Dosages may be provided, e.g., in a liquid form suitable for parenteral administration (e.g., intravenous), or a form suitable for oral administration, e.g., tablets or capsules, and the effective dose may be provided in one or more tablets, capsules or the like. In some embodiments, the anti-metabolite is administered simultaneously with radiation.

The terms "antibody" and "antibodies" as used herein is inclusive of all types of immunoglobulins, including IgG, IgM, IgA, IgD, and IgE, or fragments thereof, that may be appropriate for the medical uses disclosed herein. The antibodies may be monoclonal or polyclonal and may be of any species of origin, including, for example, mouse, rat, rabbit, horse, or human. Antibody fragments that retain specific binding to the protein or epitope, for example, CTLA4, PDL1 or PD1, bound by the antibody used in the present invention are included within the scope of the term "antibody." Such fragments can be produced by known techniques. The antibodies may be chimeric or humanized, particularly when they are used for therapeutic purposes. The antibody may be obtained or prepared using methods known in the art.

"Antibody therapy" refers to the medical use of antibodies that bind a target cell or protein to treat cancer and/or stimulate an immune response in a subject that results in the recognition, attack and/or destruction of cancerous cells in the subject, and in some embodiments of the invention, to activate or stimulate a memory immune response in a subject that results in the subsequent recognition, attack and/or destruction of cancerous cells in the subject.

"CTLA4 antibody therapy" refers to the use of antibodies directed toward cytotoxic t-lymphocyte antigen 4 (anti-CTLA4) in modulating an immune response in a subject. In some embodiments, the CTLA4 antibody inhibits or blocks the action of CTLA4 signaling that results in the inhibition of T-cell activation in the attack and destruction of cancer cells. Suitable antibodies for this use include, but are not limited to, antibodies that are CTLA4 antagonists or the CTLA4 antibodies as set forth in U.S. Pat. Nos. 8,685,394 and 8,709,417. Some embodiments of the antibody include MDX-010 (ipilimumab, Bristol-Myers Squibb) and CP-675,206 (tremelimumab, Pfizer). In a particular embodiment, the antibody is ipilimumab.

"PDL1 antibody therapy" refers to the use of antibodies directed toward programmed death ligand 1 (anti-PDL1) in modulating an immune response in a subject. In some embodiments, the PDL1 antibody inhibits or blocks the interaction of PDL1 with programmed cell death protein 1 (PD1), wherein the blockage of the interaction between PDL1 and PD1 inhibits the negative regulation of T-cell activation by PD1 to attack and destroy cancer cells. Suitable antibodies for this use include, but are not limited to, the antibodies set forth in U.S. Pat. Nos. 8,217,149, 8,383,796, 8,552,154 and 8,617,546. In a particular embodiment, the antibody is MPDL3280A (Roche).

"PD1 antibody therapy" refers to the use of antibodies directed toward programmed cell death protein 1 PD1 (anti-PD1) in modulating an immune response in a subject. In some embodiments, the PD1 antibody inhibits or blocks the interaction of PD1 with PDL1, wherein the inhibition or blockage of the interaction between PDL1 and PD1 inhibits the negative regulation of T-cell activation by PD1 to attack and destroy cancer cells. Suitable antibodies for this use include, but are not limited to, the antibodies set forth in U.S. Pat. Nos. 7,029,674, 7,488,802, 7,521,051, 8,008,449, 8,354,509, 8,617,546 and 8,709,417. Particular embodiments of the antibody include MDX-1106 (nivolumab, Bristol-Myers Squibb), labrolizumab (Merck), and pembrolizumab (KEYTRUDA®, Merck).

"Anti-metabolite chemotherapy" refers to the use of an anti-metabolite chemotherapeutic in the treatment of a subject. "Anti-metabolite" refers to a group of molecules that impede DNA and RNA synthesis. Examples of anti-metabolites include, but are not limited to, anti-folates, fluoropyrimidines, deoxynucleoside analogues and thiopurines. Anti-folates include methotrexate and pemetrexed. Fluoropyrimidines include fluorouracil and capecitabine. Deoxynucleoside analogues include cytarabine, gemcitabine, decitabine, 5-azacytidine (VIDAZA), fludarabine, nelarabine, cladribine, clofarabine and pentostatin. Thiopurines include thioguanine and mercaptopurine. In one embodiment, the anti-metabolite is gemcitabine. In another embodiment, the anti-metabolite is capecitebine.

In order that the invention described herein may be more fully understood, the following examples are set forth. It should be understood that these examples are for illustrative purposes only and are not to be construed as limiting this invention in any manner.

EXAMPLES

Example 1: Combination Therapy of Er-886046 with Radiation or Antibodies

Materials and Methods

Reagents and Instruments; ER-886046 was generated by Eisai Inc. (Andover, Mass.). The in vivo ready antibody against CTLA4 (clone 9H10) and its isotype control were obtained from BioXCell (Wester Lebanon, N.H.); the antibody against PDL1 (clone 10f.9G2) and its control (clone LTF-2) were obtained from TONBO Bioscience (San Diego, Calif.); and the antibody against mouse PD1 (clone RMP1-14) and its isotype control were obtained from BioXcell (Wester Lebanon, N.H.). Methyl cellulose and collagenase I was purchased from Sigma. Fluorescence-labeled antibodies for mouse CD45 (clone 30-F11), CD8 (clone 53-6.7), CD11b (clone Ml/70), Gr1 (clone RB6-8C5) were obtained from eBioscience (San Diego, Calif.). A biological irradiator X-RAD 320 from Precision X-Ray was used for animal tumor radiation. Flow cytometric analysis was conducted using a 6-color BD Canto-1 flow cytometic machine (BD Biosciences) equipped with software FlowJo version 7.6. The IVIS spectrum was purchased from Perkin Elmer equipped with software of Living Image version 4.3.1.

Cell lines; Mouse colon CT26 cells (CRL-2638), melanoma B16F10 cells (CRL-6475) and breast 4T1 cells (CRL-2539) were purchased from American Tissue Culture Collection. Luciferase-expressing 4T1 cells (4T1-luc2) were obtained from Perkin Elmer. All cells were cultured in RPMI-1640 medium supplemented with 10% fetal bovine serum in a humidified incubator at 37° C. in a 5% carbon dioxide atmosphere and sub-cultured twice weekly until the necessary number of cells for inoculation of mice was obtained.

Animals; BalB/c and C57BL/6 female mice at 4-6 weeks in age were purchased from Charles River Laboratories. The animals were housed in microisolator cages, up to five per cage with a 12 h light/dark cycle. Cages were changed twice weekly. The animals were observed daily and clinical signs were noted. All experimental procedures were approved by the animal laboratories of Eisai Inc., or of Southern Research Institute, which are each AAALAC accredited.

Animal studies; In vitro cultured cancer cells were harvested and suspended in 100 μl of phosphate buffered saline at a cell concentration of $1.0 \times 10^5$ cells/ml and subcutaneously (sc) injected into the mice using a 26 g syringe on day 0. At the days post cell implantation as indicated in the figures, the mice were randomized based on the tumor size followed by treatments with radiation at 3 or 9 Gy dose per treatment, anti-PDL1 at 200 μg/mouse per intraperitoneal injection (ip), or anti-CTLA4 at 200 or 100 μg/mouse per ip injection with or without orally administration of ER-886046 at a dose of 150 mg/kg. The animals that were assigned to the treatment groups in individual study had close mean tumor weights in all groups. The tumor sizes were measured twice a week by a digital caliper (Mitutoyo Corp), and the volume was calculated using the formula $(1 \times w^2)/2 = mm^3$, where 1 and w refer to the larger and smaller perpendicular dimensions collected at each measurement. Graphs of group tumor sizes (mean±SEM) and body weights (mean±SEM) versus time were plotted using software GraphPad Prism 6 (Lake Forest, Calif.). Student t-test and Gehan-Breslow-Wilcoxon test were used for statistical analysis.

In case of tumor rechallenge of tumor-free mice after treatments, CT26 cells and 4T1 cells were individually sc injected into the different flanks of the same mouse, and the growth of each tumor was measured and graphed as described above. Naïve mice that received neither cancer cell injection nor drug treatment were included as controls. In the lung metastasis of 4T1-luc2 model, the cells were inoculated and the tumor-bearing mice were radomized on day-10 based on the size of primary tumors. At the end of study on day 27, the mice in all treatment groups were intranasally administered luciferin and the lungs were resected and analysed for luciferase expression using IVIS instrument. Quantification of the luciferase activity in the lungs was achieved by software Living Image.

Flow cytometry; CT26 tumors with or without treatments received were surgically resected and minced by physical pressure, followed by digestion with collagenase I at 1 mg/ml at 37° C. for 1 h. The single cell mixtures from the digestion were labelled by incubation with fluorescent antibodies against immune cell antigens and analysed by flow cytometry. Cell population calculation was performed by software FlowJo 7.6.

Results

Figure 1B:
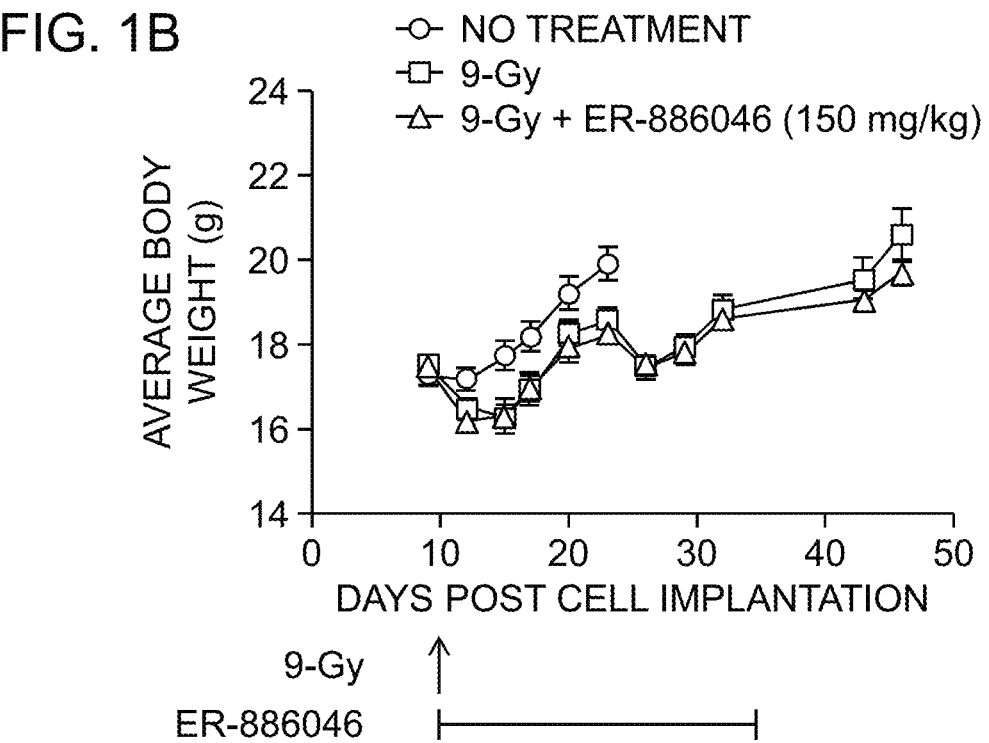

Improved anti-tumor activity by combination therapy of ER-886046 and radiation compared to radiation alone. To investigate whether treatment with ER-886046 enhances the anti-tumor effect of radiation, CT26 tumors that were grown subcutaneously in mice were treated with local radiation at a dose of 9 Gy on day-9 after tumor implantation followed by a daily oral administration of ER-886046 for a period of 4 weeks. FIG. 1A shows the average tumor sizes of the treatment groups. Radiation alone showed significant tumor growth inhibition in the period of days 9-32, followed by a rapid tumor regrowth compared with control group. In contrast, treatment with ER-886046 and radiation produced sustained tumor growth inhibition until the end of the study on day 49, where no significant tumor growth was noticed in comparison with the tumor size before the treatments. The anti-tumor activity of the combination group was statistically significantly improved as compared to the radiation alone. Addition of ER-886046 to the treatment regime did not impact the gross health and animal body weight as compared to the radiation alone (FIG. 1B).

Figure 2A:
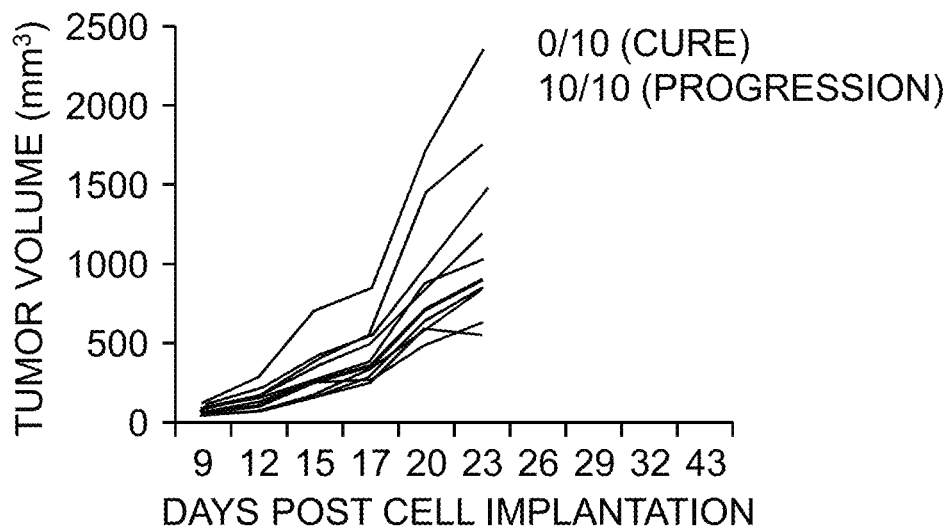
FIG. 2A to FIG. 2C. Tumor growth plots of the individual CT-26 tumors treated with radiation/ER-886046 or radiation alone. The animals are of the experiment described in FIG. 1A and FIG. 1B. Panel shown in FIG. 2A) Vehicle treatment group. Panel shown in FIG. 2B) Radiation. Panel shown in FIG. 2C) Radiation plus ER-886046. N=10-12 per group. Cure, complete tumor regression; Progression, fast tumor growth; Stable, comparable size from initial tumors before the treatment. Radiation treatment: 9 Gy single dose on day 9; ER-886046 dosing: 150 mg/kg, oral (po) administration daily from day 9 to day 32. Each line represents an individual animal.
Figure 2B:
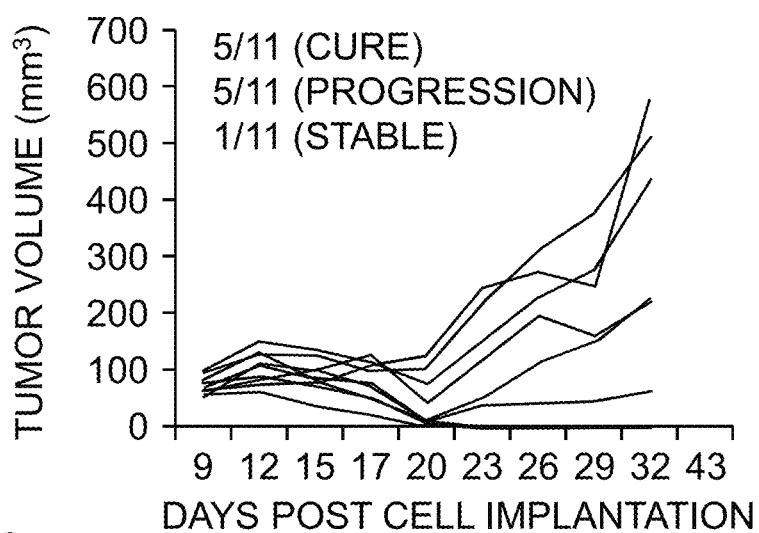
Figure 2C:
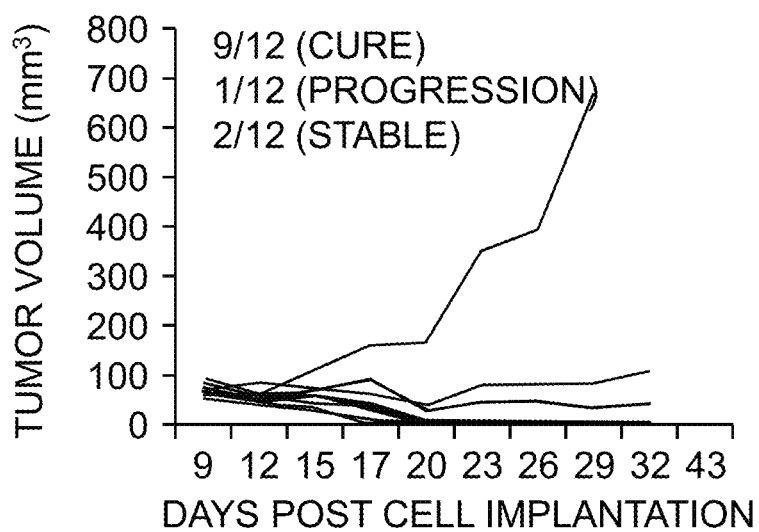
Figure 3:
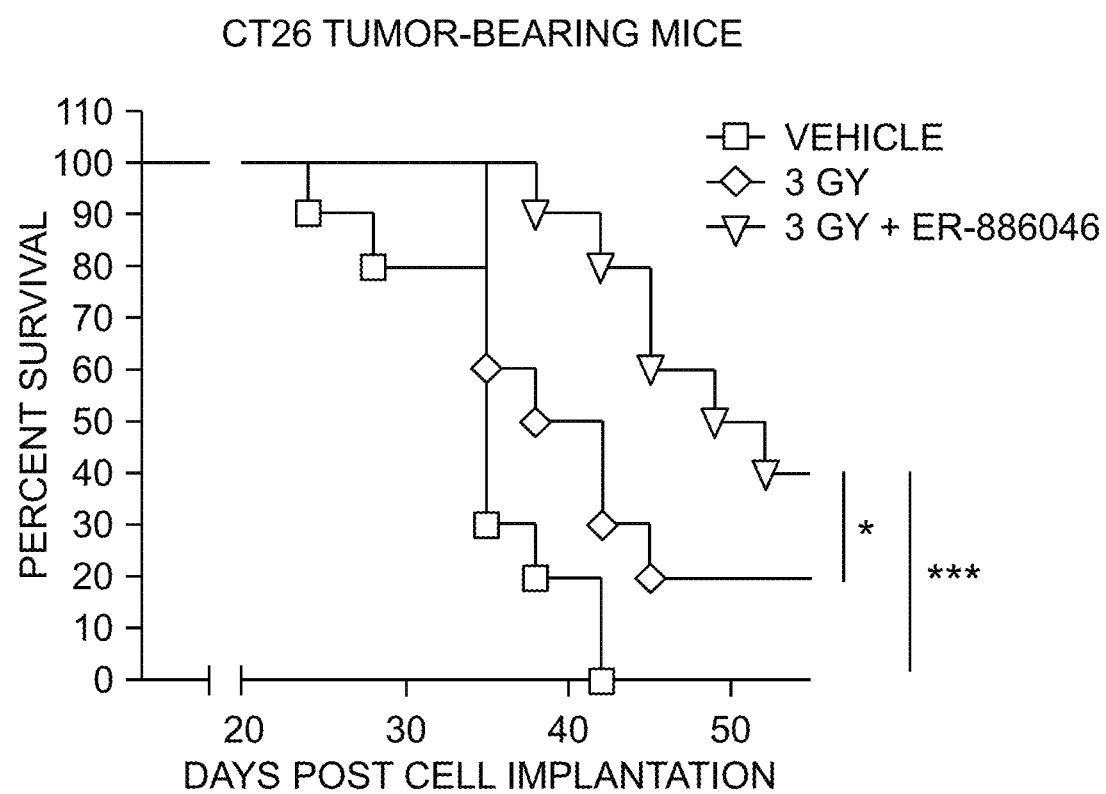
FIG. 3. Improved tumor growth suppression and animal survival by low dose radiation/ER-886046 compared with low dose radiation alone. Plots of animal survival status among indicated treatment groups. Radiation treatment: 3 Gy single dose on day 17; ER-886046 dosing: 150 mg/kg, po administration daily from days 17 to 45. Once an animal reached 20% weight loss compared its initial body weight or had a tumor volume equal to or higher than 2000 mm$^3$, the animal was removed from the study according to the protocol. N=10 per group. *, p<0.05; ***, p<0.001; Gehan-Breslow-Wilcoxon test.

By comparing growth curves of the individual tumors of the treatment groups (FIG. 2A, FIG. 2B, and FIG. 2C), it was found that combination of ER-886046 and radiation resulted in cure in 9 out of 12 mice, and only 1 out of 12 tumors had fast progression. In contrast, only 5 out of 11 mice were tumor-free at the end of study by radiation treatment alone. Furthermore, combination of a low dose of single radiation at 3 Gy with ER-886046 significantly increased the animal survival compared with either vehicle treatment or radiation treatment alone (FIG. 3). Taking these results together, addition of oral administration of ER-886046 to the radiation treatment significantly enhanced the anti-tumor activity of radiation at both high and low doses in the preclinical animal model.

Figure 4A:
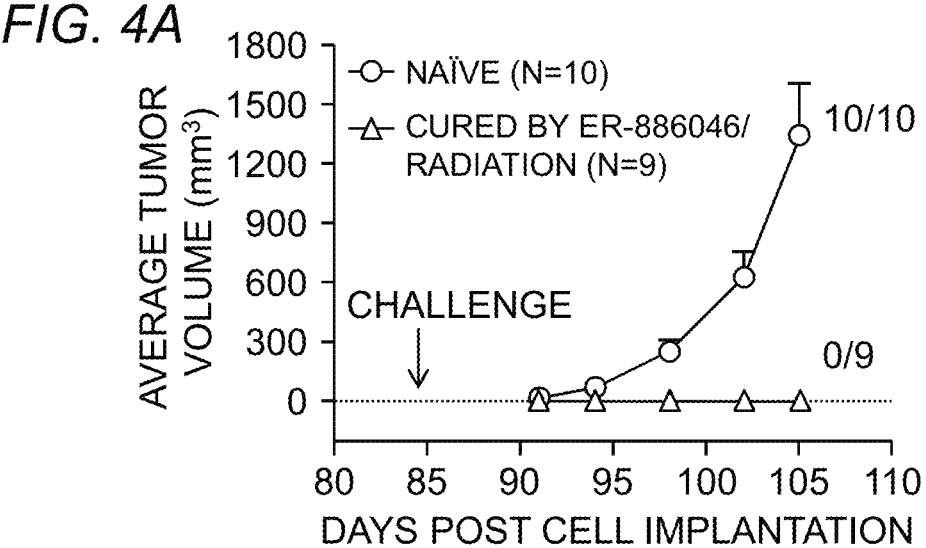
FIG. 4A to FIG. 4C. Long lasting anti-tumor effect with a memory immune response by ER-886046/radiation treatment. Panel shown in FIG. 4A) Tumor growth in the cured mice by ER-886046 and radiation combination treatment or in the naïve BalB/c mice that received injection of CT26 cells. Panel shown in FIG. 4B) Tumor growth of secondarily challenged CT-26 tumors in the cured mice or in naïve mice. Panel shown in FIG. 4C) Growth of 4T1 tumors in cured mice or in naïve mice. N=9-10. Note the complete rejection of challenged CT-26 tumor and reduced growth of challenged 4T1 tumors in the combination cured mice. ***, p<0.001. 2 tailed student t-test. Note that no treatment was applied to any animals.
Figure 4B:
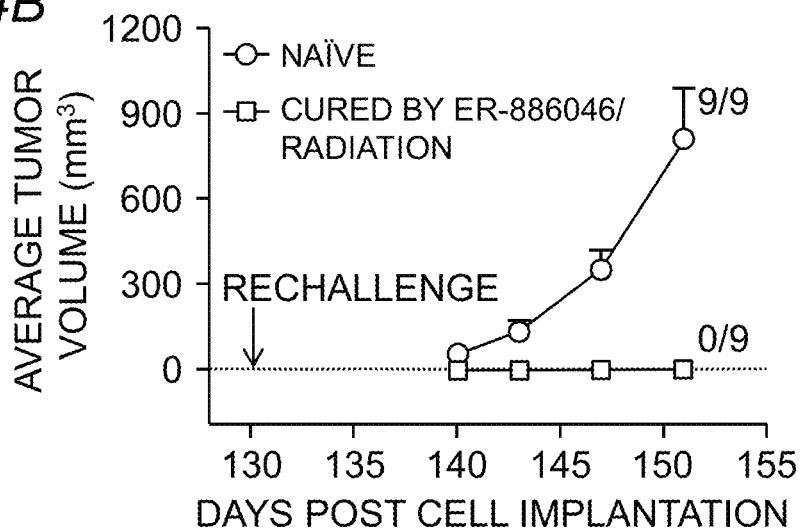
Figure 4C:
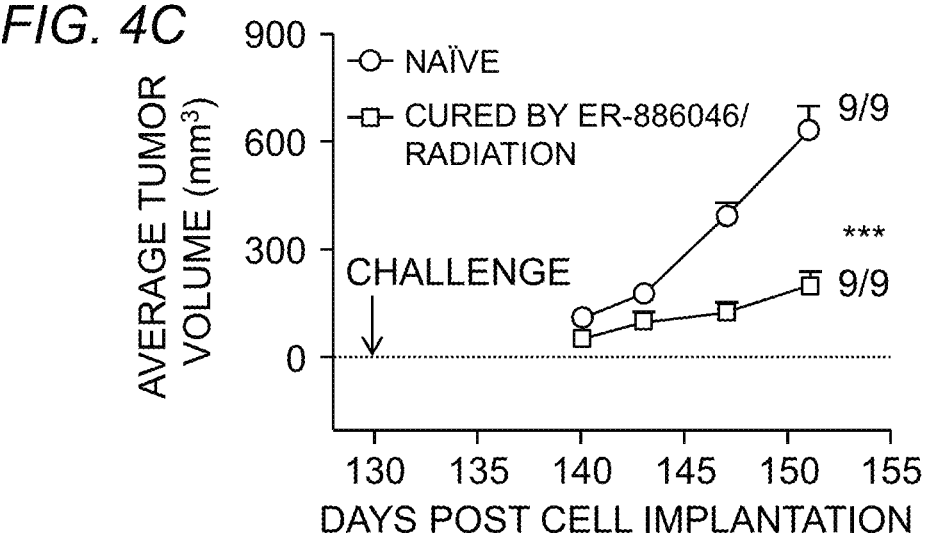

Cured mice after combination treatment with ER-886046 and radiation had a memory anti-tumor immune response. The 9 tumor-free mice from the above study were followed for an additional 2 months, at which time there was still no tumor recurrence. To test whether these tumor-free mice from the combination treatment had a memory immune response to the tumors that were rejected, the same CT26 cell line was injected at another site of the mice and the tumor growth was monitored for the following 1.5 months. Strikingly, all of the mice that received challenge did not grow tumors at all. In contrast, injection of the same amount of CT26 cells in the age-matched animals produced fast-growing tumors (FIG. 4A). Moreover, secondary challenge of CT26 cells 1.5 months after the first challenge, again, did not produce detectable tumor in the cured mice (FIG. 4B). Interestingly, injection of another, very different tumor cell line, 4T1, to the cured mice showed no rejection of the tumor, but the growth rate was significantly reduced compared to the control group (FIG. 4C). These results clearly indicated that the cured mice by the combination treatment of ER-886046 and radiation had generated a tumor antigen specific memory immune response. The growth inhibition of 4T1 tumors in the cured mice indicates the existence of an epitope spreading effect in the cured mice, which is a very favorable effect for tumor patients.

Abscopic effect of the combination treatment of ER-886046 and radiation in an animal model. Induction of anti-tumor immune response can be systemic and thus highly valuable for treating metastatic cancer, which has multiple lesions in one host. To mimic the large metastatic lesions in mice, we simultaneously grew CT26 tumors on both sides of an individual mouse by subcutaneously injecting cancer cells. The tumors on the right side of the mice were treated with both radiation and ER-886046. The tumors on the left side of the mice received ER-886046 only. Measurements of the tumors on the right side of the mice that received both radiation and ER-886046 showed better tumor growth suppression compared with those that received radiation alone or ER-886046 alone (FIG. 5A). Moreover, tumors on the left side of the mice, that received no radiation and only ER-886046, showed a significantly reduced tumor growth rate compared with those receiving no ER-886046 treatment (FIG. 5B). These results demonstrated that the combination of local radiation and systemic ER-886046 administration inhibited the growth of a tumor that was not radiated, and thus indicating an abscopic effect on the growth of metastatic tumors.

Figure 6A:
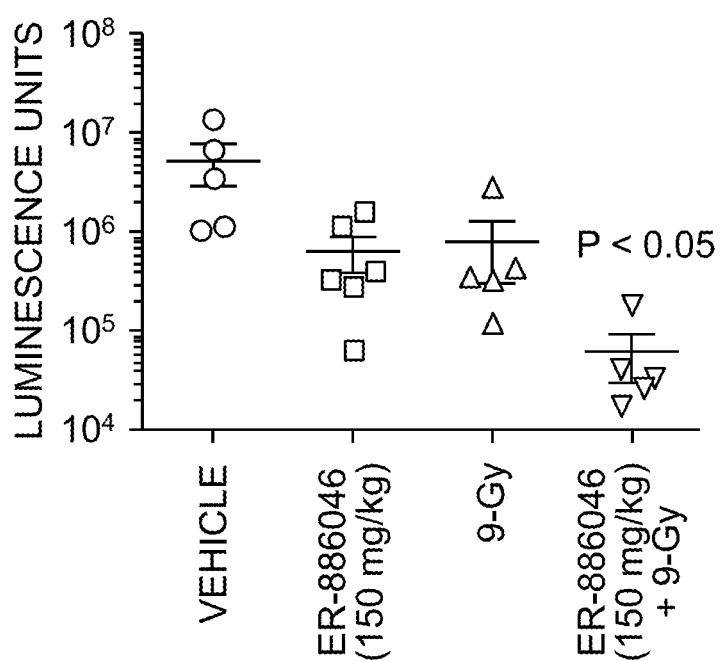
FIG. 6A to FIG. 6B. Anti-pulmonary metastasis activity of ER-886046/radiation in breast 4T1 tumor model. 4T1-luc2 cells were subcutaneously (sc) inoculated into the BalB/c mice. When the average size of tumors reached 100 mm$^3$, the tumors were radiated with a dose of 9 Gy once with or without daily oral administration of ER-886046 at dose of 150 mg/kg. Panel shown in FIG. 6A) At the end of study on day 27, lung metastasis of the animals was analyzed and quantified by luciferase expression. Panel shown in FIG. 6B) Representative IVIS images of each group are shown. Student t-test was used for statistic analysis.
Figure 6B:
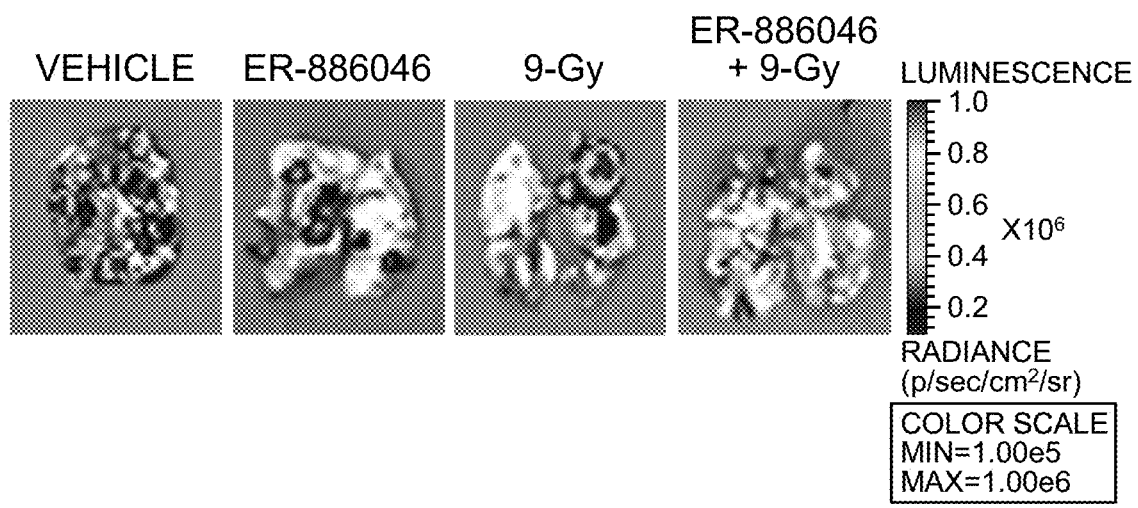
Figure 7A:
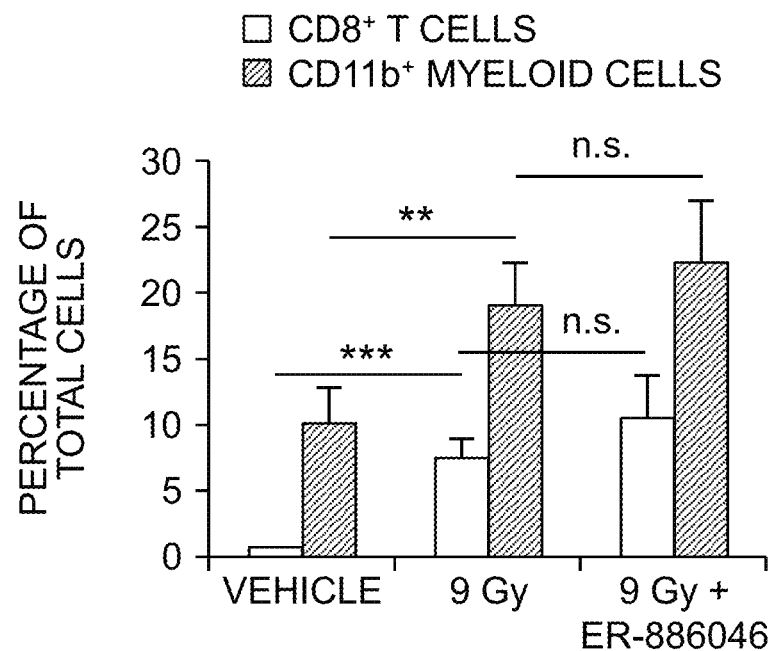
FIG. 7A to FIG. 7B. Radiation and ER-886046 worked synergistically to modify the intratumoral immunity. Panel shown in FIG. 7A) Quantification of myeloid cells (CD11b$^+$) and cytotoxic T cells (CD8$^+$) in the CT26 tumors that received 9 Gy alone, 9 Gy+ER-886046, or vehicle alone. Panel shown in FIG. 7B) Quantification of myeloid-derived suppressor cells (MDSC cells, CD11b$^+$Gr1$^+$) in the tumors. Radiation was given once to the tumors on the day of randomization, while ER-886046 was administered po daily administrated at 150 mg/kg to the animals for 7 consecutive days after randomization. The tumors were analyzed by flow cytometry one day after the last dose of ER-886046. **, p<0.01; ns, not significant; student t-test.
Figure 7B:
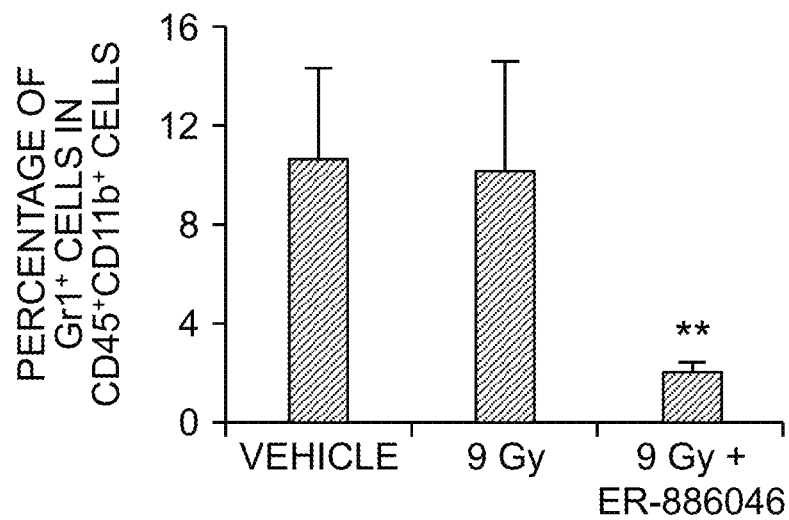

Anti-spontaneous metastatic effect of ER-886046 and radiation combination therapy. To test whether combination of ER-886046 and radiation has an anti-metastasis effect, luciferase-expressing mouse breast 4T1-luc2 tumors were grown subcutaneously in Ba1B/c mice. The primary tumors were treated with vehicle, ER-886046, single radiation at 9 Gy, and combination of ER-886046 and radiation. Treatment on radiation was given on day-9, and ER-886046 was orally administered daily from days 9-27. At day 27, the mice in all treatment groups were intranasally administered luciferin and the lungs were resected and analyzed for luciferase expression. Quantification of the luciferase expression showed a significant reduction in the combination treatment only (FIG. 6A and FIG. 6B) indicating of a reduced spontaneous lung metastasis.

Altered intratumoral immune cell infiltration by combination treatment of ER-886046 and radiation. To investigate the impact of the combination treatment of ER-886046 and radiation in intratumoral immunity, immune cells in the CT26 tumors that received combination treatment or radiation alone were analyzed by flow cytometry. Radiation alone significantly increased the tumor infiltration frequency of both $CD8^+$ T cells and $CD11b^+$ myeloid cells, and addition of ER-886046 to radiation had no additional significant effect in the frequency of both cell types. On the other hand, only the combination treatment reduced the ratio of $Gr1^+$ cells among $CD45^+CD11b^+$ cells, indicating a reduced frequency of the myeloid derived suppressor cells by a combined treatment of ER-886046 and radiation compared with those of vehicle or radiation alone.

Figure 8A:
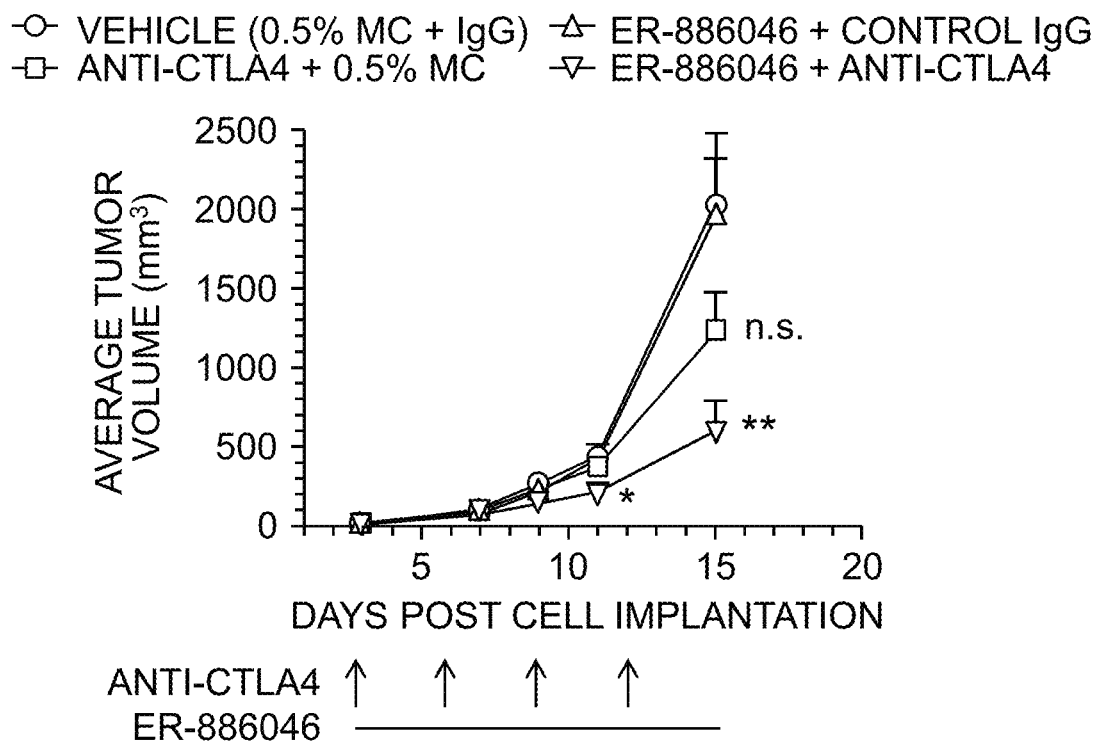
FIG. 8A to FIG. 8B. Synergistic anti-tumor activity of ER-886046 with anti-CTLA4 in B16F10 tumors. Panel shown in FIG. 8A) Anti-tumor growth activities of anti-CTLA4 and ER-886046 in B16F10 melanoma tumors growing in C57BL/6 mice. Panel shown in FIG. 8B) Animal body weight changes of the treatment groups. Anti-CTLA4 dosing: 200 μg for the first intravenous (iv) injection on day 3 after transplantation and 100 μg for the other three iv injections on days 6, 9 and 12 as indicated by the arrows. ER-886046 dosing: 150 mg/kg, po daily administration from day 3 to day 15 as indicated by the bars. *, p<0.05; **, p<0.01; ns, not significant; student t test.
Figure 8B:
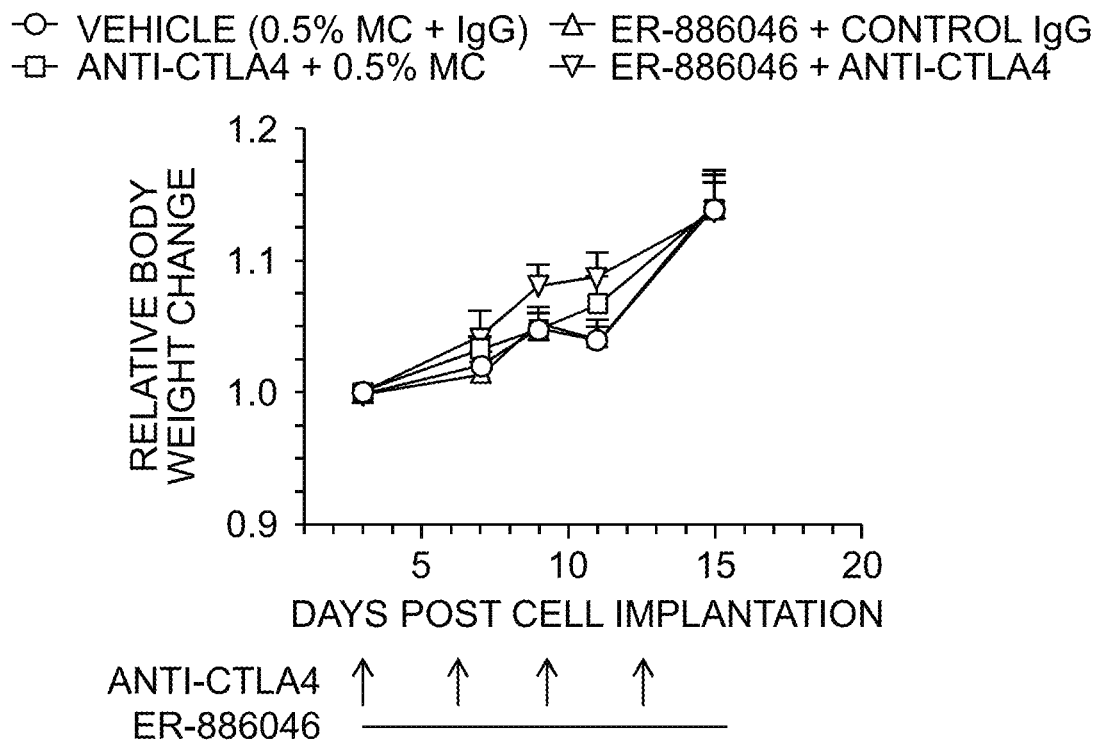

Synergistic anti-tumor activity of ER-886046 and anti-CTLA4 in a preclinical model. Anti-CTLA4 (Ipilimumab) is now an approved immune therapy for metastatic melanoma, which blocks CTLA4 signaling in immune cells, especially the T cells. To investigate whether treatment with ER-886046 influences the anti-tumor activity of anti-CTLA4, we tested the effects of combination therapy of ER-886046 and anti-CTLA4 in a mouse melanoma B16F10 model. As shown in FIG. 8A, ER-886046 alone had minimal activity in this model, and anti-CTLA4 alone showed some but non-statistically significant activity. However, combination of ER-886046 and anti-CTLA4 treatment showed a highly significant anti-tumor activity. No animal body weight loss was observed for the combination therapy treatments. The results indicated a synergistic anti-tumor activity for the combination of ER-886046 and anti-CTLA4 therapy in the preclinical model.

Figure 9A:
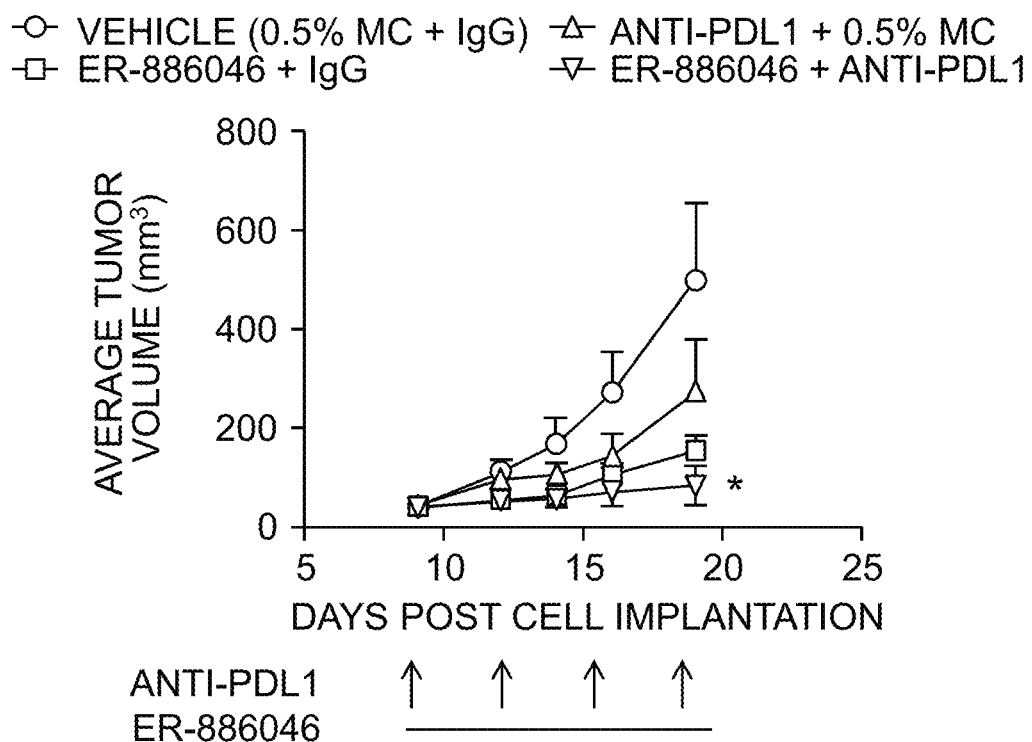
FIG. 9A to FIG. 9B. Enhanced anti-tumor activities of anti-PDL1 or anti-PD1 by ER-886046 in CT26 tumors. Panel shown in FIG. 9A) Activities of anti-PDL1 plus ER-886046 and anti-PDL1 alone. Anti-PDL1 dosing: 200 μg per iv injection on days 9, 12, 15 and 18 post cell implantation as indicated by the arrows; ER-886046 dosing: 150 mg/kg, po daily administration from day 9 to day 19 post cell implantation as indicated by the bar. Panel shown in FIG. 9B) Activities of anti-PD1 plus ER-886046 and anti-PD1 alone. Anti-PD1 dosing: 200 μg per iv injection on days 9, 12, 15, 18 and 21 post cell implantation as indicated by the arrows; ER-886046 dosing: 150 mg/kg, po daily administration from day 9 to day 23 post cell implantation as indicated by the bar. *, p<0.05; ***, p<0.001; student t-test.
Figure 9B:
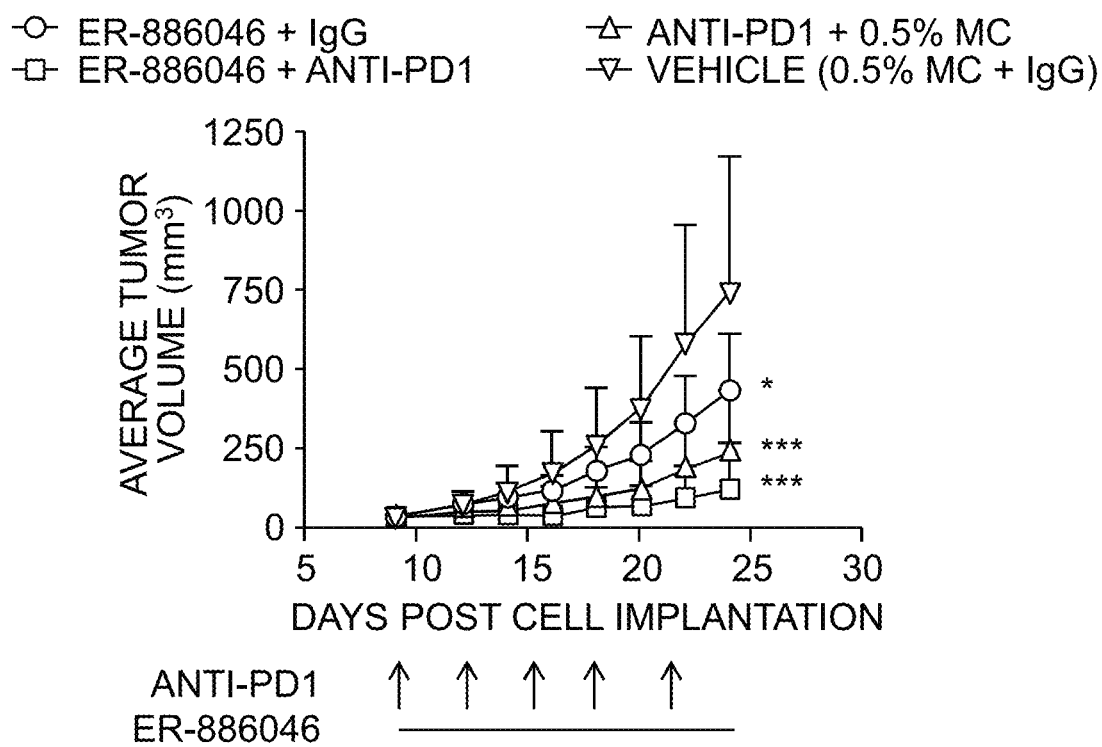

ER-886046 enhanced efficacy of anti-PD1 and anti-PDL1 cancer immune therapies in a preclinical model. Anti-PD1 and anti-PDL1 are currently in clinical trials for potential cancer immune therapeutic use. To explore potential combination effect of ER-886046 with either agent, we tested the combination therapies in CT-26 tumor model. Anti-PDL1 showed some but non-significant anti-tumor growth activity (FIG. 9A), while anti-PD1 displayed significant activity by itself (FIG. 9B). In both situations, addition of ER-886046 produced better anti-tumor activity compared to anti-PD1 or anti-PDL1 alone indicates a benefit of having the combination of ER-886046 and these antibody-based immune therapies for cancer management.

Conclusion

Combination of ER-886046 with radiation, anti-CTLA4, anti-PDL1, or anti-PD1 had significant anti-tumor activity in preclinical animal models. Inclusion of ER-886046 in the combination treatments enhanced the tumor growth suppression and even tumor rejection compared to a single agent or method alone and thus can have therapeutic use in clinic for treating cancer patients.

Example 2: Combination Therapy of Er-886046 with Radiation and Anti-Metabolite Chemotherapy Materials and Methods Reagents and Instruments; ER-886046 (Chen et al. British J Pharmacol, (2010) 160, 292-310), a specific prostaglandin $E_2$ receptor 4 antagonist, was generated by Eisai Inc. (Andover, Mass.). Gemcitabine hydrochloride and methyl cellulose were purchased from Sigma (St Louis, Mo.). A biological irradiator X-RAD 320 from Precision X-Ray was used for animal tumor radiation.

Cell lines and Animals; Mouse colon CT26 cells and pancreatic PAN02 cells were purchased from American Tissue Culture Collection and National Cancer Institute DCTD Repository, respectively. Cells were cultured in RPMI-1640 medium supplemented with 10% fetal bovine serum in a humidified incubator at 37° C. in a 5% carbon dioxide atmosphere and sub-cultured twice weekly until the necessary number of cells for inoculation of mice was obtained. Ba1B/c and C57BL/6 female mice at 4-6 weeks in age were purchased from Charles River Laboratories. The animals were housed in microisolator cages, up to five per cage with a 12 h light/dark cycle. Cages were changed twice weekly. The animals were observed daily and clinical signs were noted. All experimental procedures were approved by the Institutional Animal Care and Use Committee of Eisai Inc. The animal laboratories are AAALAC accredited.

Animal studies; In vitro cultured cancer cells were harvested and suspended in 100 µl of cold HBSS buffer at cell concentrations of $1.0 \times 10^6$ cells/ml (CT-26 cells) or of $1.0 \times 10^7$ cells/ml (PAN02 cells) and subcutaneously (sc) injected into the mice using a 26 g syringe on day 0. At the dates as indicated in the figures, the mice were randomized based on the tumor size followed by treatments with local radiation alone, gemcitabine alone (intravenous administration), ER-886046 alone (oral administration), or combinations of these treatments. The animals that were assigned to the treatment groups in individual study had close mean tumor weights in all groups. The tumor sizes were measured twice a week by a digital caliber (Mitutoyo Corp), and the volume was calculated using the formula $(1 \times w^2)/2 = mm^3$, where 1 and w refer to the larger and smaller perpendicular dimensions collected at each measurement. Graphs of group tumor sizes (mean±SEM) versus time were plotted using software GraphPad Prism 6 (Lake Forest, Calif.). Two way ANOVA was used for statistical calculation among the groups. N=8-10 in each treatment group.

In case of animal survival comparison, a tumor-bearing animal whose tumor grew to 10 bigger than the original tumor size before treatment was considered to have reached the end point and thereby removed from the study. Graphs of animal survival percentile versus time were plotted using GraphPad Prism 6, and Log-rank test was used for statistical calculation.

Results

Figure 10:
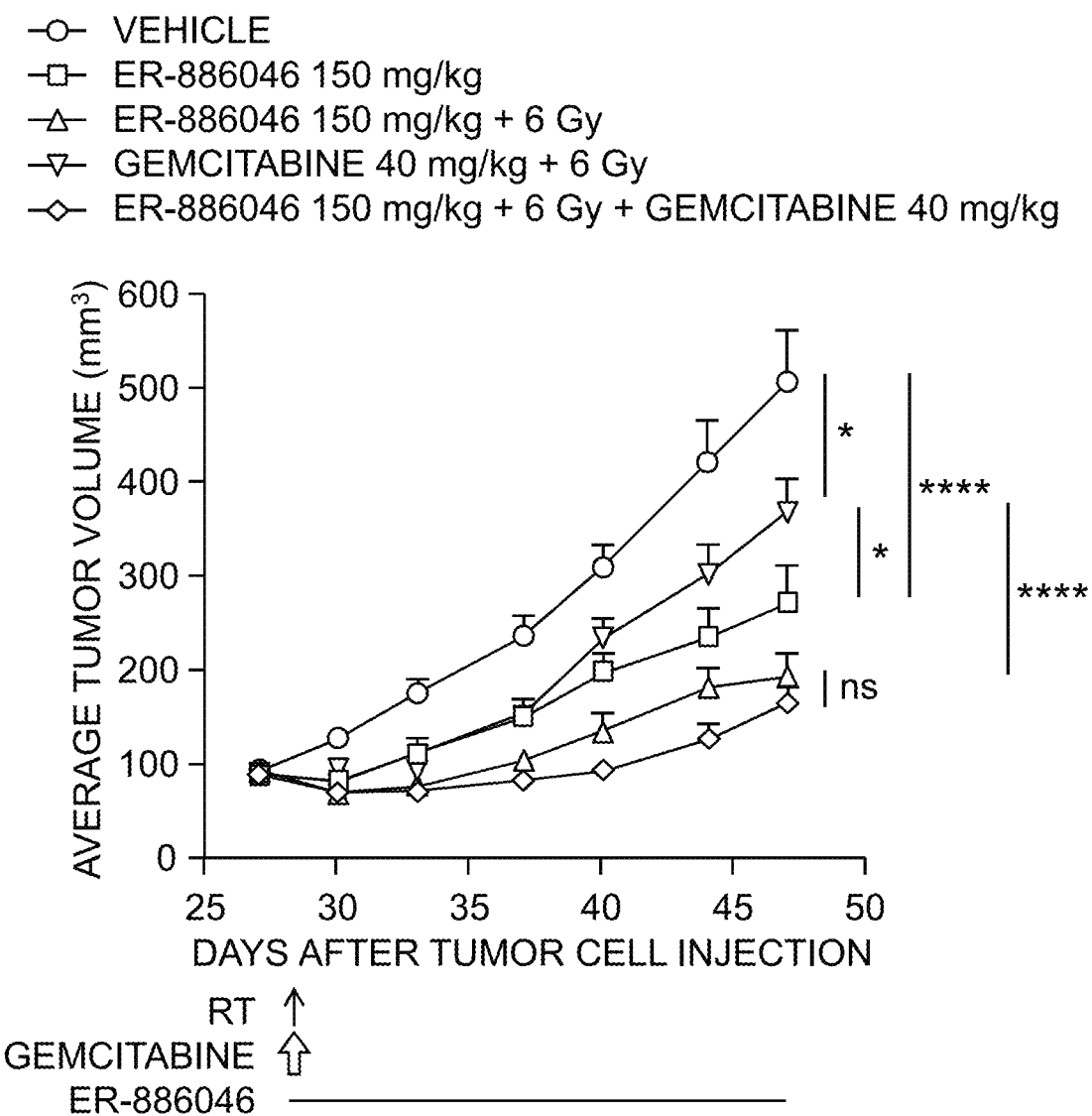
FIG. 10. Enhanced anti-tumor activity by combination therapy of ER-886046 and anti-metabolite chemotherapy with radiation compared to anti-metabolite chemotherapy with radiation alone. Antitumor activity of gemcitabine plus local radiation (RT) administered to PAN02 pancreatic tumors in C57BL/6 mice with or without ER-886046. Gemcitabine and RT dosing: a single 40 mg/kg dose of gemcitabine and a single 6 Gy dose of RT, was administered on day 27 post tumor cell injection. ER-8806046 was administered daily in an amount of 150 mg/kg from day 27 post tumor cell injection until the end of the study.

Superior anti-tumor activity by combination therapy of ER-886046 and anti-metabolite chemotherapy with radiation compared to anti-metabolite therapy with radiation alone. To evaluate whether addition of ER-886046 to anti-metabolite chemotherapy with radiation would improve anti-cancer activity in a preclinical animal model, multiple studies were carried out using murine pancreatic PAN02 tumors that grew subcutaneously in C57BL/6 mice, which received treatment with RT, and gemcitabine plus RT, both with or without ER-886046. In the first study, RT and gemcitabine were administered once on day 27 after tumor cell inoculation, while ER-886046 was given daily from day 27 until the end of the study. FIG. 10 shows the average tumor sizes of the treatment groups from this study. RT plus gemcitabine exhibited a weak but statistically significant tumor growth delay activity. ER-886046 alone was more efficacious than RT plus gemcitabine. A triple combination of ER-886046, RT and gemcitabine produced the best anti-tumor activity among the treatment groups, and the activity was significantly better than that of RT plus gemcitabine alone. Importantly, there was no significant difference in the anti-tumor activity between the triple combination group and ER-886046 plus RT group, indicating that most of the anti-tumor activity of the triple combination came from ER-886046 and RT.

In the second and third studies using the same PAN02 pancreatic cancer model, similar superior antitumor activity of the triple combination of ER-886046, RT and gemcitabine was observed compared to any of the single agent treatments or a combination of gemcitabine plus RT, as shown in FIG. 11A and FIG. 11B. RT and gemcitabine were administered once on day 19 (FIG. 11A) or day 12 (FIG. 11B), whereas ER-886046 was given daily from day 19 (FIG. 11A) or day 12 (FIG. 11B) until the end of each study. Notably, five of eight tumor-bearing animals were cured by the triple combination treatment at day 36 after tumor cell inoculation, while other treatment regimens did not produce cure (FIG. 11B). These results together revealed a synergy between ER-886046 and gemcitabine plus RT in containing and/or rejecting established tumors in a preclinical model.

All the treatments in these three studies were well tolerated without any deaths or significant body weight loss.

CONCLUSION

The data provide evidence that the combination of ER-886046 and anti-metabolite chemotherapy with radiation had significant anti-tumor growth activity in immunocompetent animal cancer models. Combination treatment of ER-886046 plus anti-metabolite chemotherapy with radiation significantly enhanced the anti-tumor activity compared with treatment with anti-metabolite chemotherapy with radiation alone, and thus can have therapeutic use in the clinic for treating cancer.

We claim:

1. A method of treating a subject having colorectal cancer or melanoma or pancreatic cancer, comprising administering to the subject, an EP4 antagonist in combination with an antibody therapy, wherein the EP4 antagonist is:

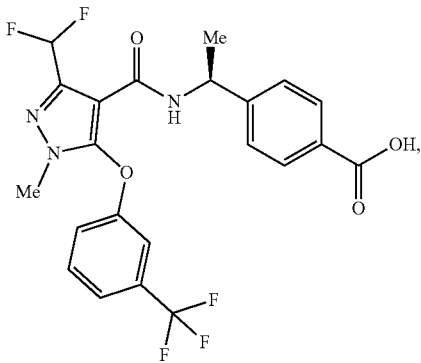 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

2. The method of claim 1, wherein said treating comprises an abscopal effect.

3. The method of claim 1, wherein the antibody therapy is CTLA4 antibody therapy.

4. The method of claim 1, wherein the subject has colorectal cancer.

5. The method of claim 1, wherein the cancer is metastatic cancer.

6. A method of generating a memory immune response in a subject having colorectal cancer or melanoma or pancreatic cancer, comprising administering to the subject, an EP4 antagonist in combination with an antibody therapy, and wherein the EP4 antagonist is:

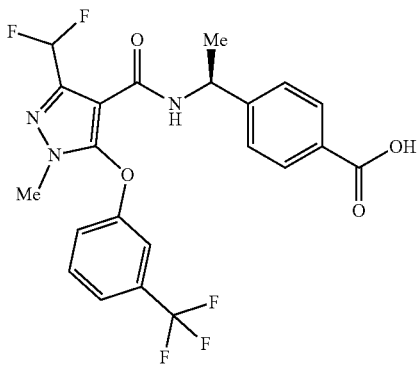 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

7. The method of claim 6, wherein said generating the memory immune response comprises an abscopal effect.

8. The method of claim 6, wherein the antibody therapy is CTLA4 antibody therapy.

9. The method of claim 6, wherein the subject has colorectal cancer.

10. The method of any of claim 6, wherein the cancer is metastatic cancer.

11. The method of claim 6, wherein the memory immune response comprises epitope spreading.

12. The method of claim 1, wherein the method further comprises administering an anti-metabolite chemotherapy in combination with the EP4 antagonist and antibody therapy.

13. A method of treating a subject having colorectal cancer or melanoma or pancreatic cancer, comprising administering to the subject, an EP4 antagonist in combination with an anti-metabolite chemotherapy, wherein the EP4 antagonist is:

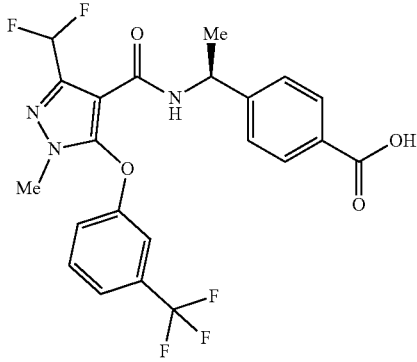 [SMILES: C[C@H](NC(=O)c1c(C(F)F)nn(C)c1Oc1cccc(C(F)(F)F)c1)c1ccc(C(=O)O)cc1]

or a pharmaceutically acceptable salt thereof.

14. The method of claim 6, wherein the memory immune response further comprises administering an anti-metabolite chemotherapy in combination with the EP4 antagonist and antibody therapy.

15. The method of claim 1, wherein the antibody therapy is PDL1 antibody therapy.

16. The method of claim 1, wherein the antibody therapy is PD1 antibody therapy.

17. The method of claim 6, wherein the antibody therapy is PDL1 antibody therapy.

18. The method of claim 6, wherein the antibody therapy is PD1 antibody therapy.

19. The method of claim 1, wherein the subject has melanoma.

20. The method of claim 1, wherein the subject has pancreatic cancer.

21. The method of claim 6, wherein the subject has melanoma.

22. The method of claim 6, wherein the subject has pancreatic cancer.

* * * * *